(12) United States Patent
Moussy et al.

(10) Patent No.: US 10,392,373 B2
(45) Date of Patent: Aug. 27, 2019

(54) OXAZOLE DERIVATIVES THAT INHIBIT SYK

(71) Applicant: AB Science, Paris (FR)

(72) Inventors: Alain Moussy, Paris (FR); Abdellah Benjahad, Champigny sur Marne (FR); Didier Pez, Nievroz (FR); Claire Schalon, Gif-sur-Yvette (FR); Franck Sandrinelli, Balan (FR); Jason Martin, L'Hay-les-Roses (FR); Willy Picoul, Lyons (FR); Emmanuel Chevenier, Limours (FR)

(73) Assignee: AB Science, Paris (FR)

( * ) Notice: Subject to any disclaimer, the term of this patent is extended or adjusted under 35 U.S.C. 154(b) by 0 days.

(21) Appl. No.: 15/760,362

(22) PCT Filed: Sep. 16, 2016

(86) PCT No.: PCT/EP2016/071930
§ 371 (c)(1),
(2) Date: Mar. 15, 2018

(87) PCT Pub. No.: WO2017/046302
PCT Pub. Date: Mar. 23, 2017

(65) Prior Publication Data
US 2019/0055230 A1    Feb. 21, 2019

(30) Foreign Application Priority Data
Sep. 18, 2015  (EP) .................... 15185910

(51) Int. Cl.
*C07D 413/14* (2006.01)
*A61K 31/513* (2006.01)
*A61K 31/506* (2006.01)
*A61K 31/5377* (2006.01)

(52) U.S. Cl.
CPC .......... *C07D 413/14* (2013.01); *A61K 31/506* (2013.01); *A61K 31/513* (2013.01); *A61K 31/5377* (2013.01)

(58) Field of Classification Search
CPC ........................... C07D 413/14; A61K 31/513
See application file for complete search history.

(56) References Cited

FOREIGN PATENT DOCUMENTS

| WO | WO 2011/075560 | 6/2011 |
|---|---|---|
| WO | WO 2011/086085 | 7/2011 |

OTHER PUBLICATIONS

European Search Report mailed by the European Patent Office in EP App. No. 15185910.5 dated Nov. 13, 2015 (6 pages).

*Primary Examiner* — Karen Cheng
(74) *Attorney, Agent, or Firm* — Klarquist Sparkman, LLP

(57) ABSTRACT

The present invention is concerned with substituted oxazole derivatives that selectively modulate, regulate, and/or inhibit signal transduction mediated by certain native and/or mutant protein kinases implicated in a variety of human and animal diseases such as cell proliferative, metabolic, autoimmune, allergic, hematological, inflammatory and degenerative disorders. In particular, the compounds of the invention are Syk inhibitors. The invention also relates to a process for manufacturing the compounds of the invention.

15 Claims, No Drawings

OXAZOLE DERIVATIVES THAT INHIBIT SYK

CROSS REFERENCE TO RELATED APPLICATIONS

This is the U.S. National Stage of International Application No. PCT/EP2016/071930, filed Sep. 16, 2016, which was published in English under PCT Article 21(2), which in turn claims the benefit of EP Application No. 15185910.5, filed Sep. 18, 2015. The prior application is incorporated herein in its entirety.

FIELD OF INVENTION

The present invention relates to substituted oxazole derivatives that selectively modulate, regulate, and/or inhibit signal transduction mediated by certain native and/or mutant protein kinases implicated in a variety of human and animal diseases such as cell proliferative, metabolic, autoimmune, allergic, hematological, inflammatory and degenerative disorders. In particular, these compounds are potent and selective spleen tyrosine kinase (Syk) inhibitors. The present invention further relates to a process for the manufacturing of the compounds of the invention.

BACKGROUND OF INVENTION

Protein Kinases are receptor type or non-receptor type proteins, which transfer the terminal phosphate of ATP to aminoacid residues, such as tyrosine, threonine, serine residues, of proteins, thereby activating or inactivating signal transduction pathways. These proteins are known to be involved in many cellular mechanisms, which in case of disruption, lead to disorders such as abnormal cell proliferation and migration as well as inflammation.

As of today, there are over 500 known Protein kinases. Included are the well-known Abl, Akt1, Akt2, Akt3, ALK, Alk5, A-Raf, Ax1, B-Raf, Brk, Btk, Cdk2, Cdk4, Cdk5, Cdk6, CHK1, c-Raf-1, Csk, EGFR, EphA1, EphA2, EphB2, EphB4, Erk2, Fak, Fes, Fer, FGFR1, FGFR2, FGFR3, FGFR4, Flt-3, Fms, Frk, Fyn, Gsk3α, Gsk3β, HCK, Her2/Erbb2, Her4/Erbb4, IGF1R, IKK beta, Irak4, Itk, Jak1, Jak2, Jak3, Jnk1, Jnk2, Jnk3, KDR, Kit, Lck, Lyn, MAP2K1, MAP2K2, MAP4K4, MAPKAPK2, Met, Mer, MNK1, MLK1, mTOR, p38, PDGFRα, PDGFR β, PDPK1, PI3Kα, PI3Kβ, PI3Kδ, PI3Kγ, Pim1, Pim2, Pim3, PKC alpha, PKC beta, PKC theta, Plk1, Pyk2, Ret, ROCK1, ROCK2, RON, Src, Stk6, Syk, TEC, Tie2, TrkA, TrkB, Tyk2, VEGFR1/Flt-1, VEGFR2/Kdr, VEGFR3/Flt-4, Yes, and Zap70.

Spleen tyrosine kinase (Syk), an intracellular protein tyrosine kinase, is a key mediator of immunoreceptor signalling in a host of inflammatory cells including B cells, mast cells, macrophages, and neutrophils (Wong Br et al (2004), Expert Opin. Investig. Drugs, 13, 743-762). Syk is also widely expressed in nonhematopoietic cells like fibroblasts, breast cancer cells, colonic carcinoma cells, hepatocytes, neuronal cells, and vascular endothelial cells (Okamura S et al (1999), Oncol. Res. 11, 281-285). Originally, Syk was thought to function primarily in signaling of immunoreceptors such as Fc receptor (FcR) and B cell receptor (BCR). However, recent studies demonstrated the crucial role of Syk in the cell signaling of diverse cellular stimuli including IL-1, tumor necrosis factor-ca (TNFα), lipopolysaccharide, and p31-integrin (Yamada T et al (2001), J. Immunol., 167, 283-288). For instance, Syk can be activated by TNFα, resulting in MAPK phosphorylation and NF-κB translocation in hematopoietic cell lines (Takada Y and Aggarwal BB (2004), J. Immunol., 173, 1066-1077). IL-1-induced chemokine production in fibroblasts of nasal polyps is also mediated by Syk activation (Yamada T et al (2001), J. Immunol., 167, 283-288). Syk has emerged as a potential therapeutic target for treatment of allergic and autoimmune disorders.

Existing compounds active on protein kinases are not always endowed with satisfactory properties such as potency, selectivity, stability and solubility. Additionally, existing compounds active on protein kinases are not always endowed with satisfactory in vivo bioavailability.

The present invention discloses compounds that display potent and selective inhibitory activity on wild type and/or mutated protein kinase, in particular wild type and/or mutated tyrosine kinase, and more particularly Syk. In particular, the present invention discloses compounds for selectively modulating, regulating, and/or inhibiting signal transduction mediated by certain native and/or mutant protein kinase, and in particular tyrosine kinases implicated in a variety of human and animal diseases such as cell proliferative, metabolic, autoimmune, allergic, hematological, inflammatory and degenerative disorders. More particularly, compounds of the invention are potent and selective Syk inhibitors. More in particular, the Applicant evidenced that compounds displaying specific substitutions in oxazole derivatives are potent and selective inhibitors of Syk tyrosine kinase.

The present invention also discloses compounds that are especially stable. More particularly, compounds of the invention are stable over time and/or temperature. More particularly, compounds of the invention display in vivo stability.

The present invention further discloses compounds that are soluble in conventional excipients and/or carriers. More particularly, compounds of the invention are water-soluble.

DEFINITIONS

Unless otherwise specified, the terms below used herein are defined as follows:

The term "halogen" means fluoro, chloro, bromo, or iodo.

As used herein, the term "alkyl" or "alkyl group" means a saturated straight chain or branched non-cyclic hydrocarbon. Unless otherwise indicated, alkyl groups may have from 1 to 10, such as from 1 to 6, or from 1 to 4 carbon atoms, for example from 1 to 3 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl and 3,3-diethylhexyl.

As used herein, the term "haloalkyl" refers to any alkyl group substituted by one or more halogen atom. Examples of preferred haloalkyl groups are $CF_3$, $CHF_2$ and $CH_2F$.

As used herein, the term "aryl" or "aryl group" means a monocyclic or polycyclic-aromatic hydrocarbon radical. Unless otherwise indicated, aryl groups may have from 6 to 14 carbon atoms. Examples of suitable aryl groups include phenyl, tolyl, anthracenyl, fluorenyl, indenyl, azulenyl, and naphthyl, as well as benzo-fused carbocyclic moieties such as 5,6,7,8-tetrahydronaphthyl.

The term "cycloalkyl" or "cycloalkyl group" means a saturated or partially unsaturated, monocyclic, fused bicyclic or bridged polycyclic ring assembly. For example, cycloalkyl group may be a C3-C10 cycloalkyl group, such as C3 or C4 cycloalkyl group, such as a cyclopropyl, cyclobutyl, cyclopentyl, cyclohexyl, cycloheptyl or cyclooctyl group.

As used herein, the term "alkoxy" or "alkoxy group" refers to an alkyl group as defined above which is attached to another moiety by an oxygen atom. Examples of alkoxy groups include methoxy, isopropoxy, ethoxy, tert-butoxy.

As used herein, the term "heterocycle" refers collectively to "heterocycloalkyl groups" and "heteroaryl groups".

As used herein, the term "heterocycloalkyl" or "heterocycloalkyl group" means a monocyclic or polycyclic group having at least one (for example from one to five, such as one or two or three or four) heteroatom selected from O, N or S, and which may be saturated or unsaturated, but is not aromatic. A heterocycloalkyl may have from 2 to 11 carbon atoms. Examples of heterocycloalkyl groups including: piperidinyl, piperazinyl, N-methylpiperazinyl, 2-oxopiperazinyl, 2-oxopiperidinyl, 2-oxopyrrolidinyl, 4-piperidonyl, pyrrolidinyl, hydantoinyl, valerolactamyl, oxiranyl, oxetanyl, tetrahydropyranyl, tetrahydrothiopyranyl, tetrahydropyrindinyl, tetrahydropyrimidinyl, tetrahydrothiopyranyl sulfone, tetrahydrothiopyranyl sulfoxide, morpholinyl, thiomorpholinyl, thiomorpholinyl sulfoxide, thiomorpholinyl sulfone, 1,3-dioxolane, tetrahydrofuranyl, dihydrofuranyl-2-one, tetrahydrothienyl, and tetrahydro-1,1-dioxothienyl. Typically, monocyclic heterocycloalkyl groups have 3 to 7 ring atoms. Preferred 3 to 7 membered monocyclic heterocycloalkyl groups have 5 or 6 ring atoms. A heteroatom may be substituted with a protecting group known to those of ordinary skill in the art, for example, the hydrogen on a nitrogen may be substituted with a tert-butoxycarbonyl group.

As used herein, the term "heteroaryl" or "heteroaryl group" means a monocyclic or polycyclic heteroaromatic ring comprising carbon atom ring members and one or more heteroatom ring members (such as, for example, oxygen, sulfur or nitrogen). Typically, heteroaryl groups may have from 5 to 14, such as from 5 to 8 ring members. Typically, a heteroaryl group has from 1 to 5, such as one or two or three or four, heteroatom ring members. Typically may have from 1 to about 14 carbon atom ring members. Representative heteroaryl groups include pyridyl, 1-oxo-pyridyl, furanyl, thiophenyl, benzo[1,3]dioxolyl, benzo[1,4]dioxinyl, thienyl, pyrrolyl, oxazolyl, imidazolyl, thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, imidazo[1,2-a]pyridyl, and benzo(b)thienyl. A heteroatom may be substituted with a protecting group known to those of ordinary skill in the art, for example, the hydrogen on nitrogen may be substituted with a tert-butoxycarbonyl group. In addition, nitrogen or sulfur heteroatom ring members may be oxidized. The heteroaromatic ring may be a 5-8 membered monocyclic heteroaryl ring. The point of attachment of a heteroaromatic or heteroaryl ring to another group may be at either a carbon atom or a heteroatom of the heteroaromatic or heteroaryl rings.

As used herein the term "substituent" or "substituted" means that a hydrogen radical on a compound or group is replaced with any desired group that is substantially stable to reaction conditions in an unprotected form or when protected using a protecting group. Examples of substituents are those found in the exemplary compounds and embodiments disclosed herein, as well as halogen, alkyl or aryl groups as defined above, hydroxyl, alkoxy as defined above, nitro, thiol, heterocycloalkyl groups, heteroaryl groups, cyano, cycloalkyl groups as defined above, as well as a solubilising group, —NRR', —NR—CO—R', —CONRR', —SO$_2$NRR' group wherein R and R' are each independently hydrogen or alkyl as defined above. Examples of substituents are halogen, C1-C10 unsubstituted alkyl, C6-C14 unsubstituted aryl, hydroxyl, C1-C10 unsubstituted alkoxy, nitro, thiol, unsubstituted 3-7 membered heterocycloalkyl, unsubstituted 3-7 membered heteroaryl, cyano, C1-C10 unsubstituted cycloalkyl, a solubilising group, —NRR', —NR—CO—R', —CONRR', —SO$_2$NRR' group wherein R and R' are each independently hydrogen or C1-C10 unsubstituted alkyl. As used herein, the term "solubilising group" or "water-solubilising group" means a group which has a hydrophilic character sufficient to improve or increase the water-solubility of the compound in which it is included, as compared to an analogue compound that does not include the group. The hydrophilic character can be achieved by any means, such as by the inclusion of functional groups that ionize under the conditions of use to form charged moieties (e.g., carboxylic acids, sulfonic acids, phosphoric acids, amines, etc.); groups that include permanent charges (e.g., quaternary ammonium groups); and/or heteroatoms or heteroatomic groups.

Examples of "heteroatomic groups" are N—(CH$_2$)$_z$R'', N—(CH$_2$)$_z$—C(O)R'', N—(CH$_2$)$_z$—C(O)OR'', N—(CH$_2$)$_z$—S(O)$_2$R'', N—(CH$_2$)$_z$—S(O)$_2$OR'', N—(CH$_2$)$_z$—C(O)NR''R''', wherein
z is an integer ranging from 0 to 6, such as 0 or 1 or 2 or 3 or 4 or 5 or 6, and
R'' and R''' are each independently selected from the group consisting of: hydrogen; a C1-C10 alkyl group which is optionally substituted by one or more hetereoatom such as halogen (selected from F, Cl, Br or I), oxygen and nitrogen; a C1-C10 alkoxy group; an unsubstituted aryl, and an unsubstituted heteroaryl group.

The solubilising group may also be a moiety having one of the following structures (a)-(k):

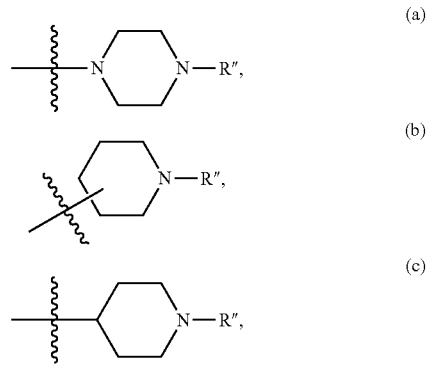

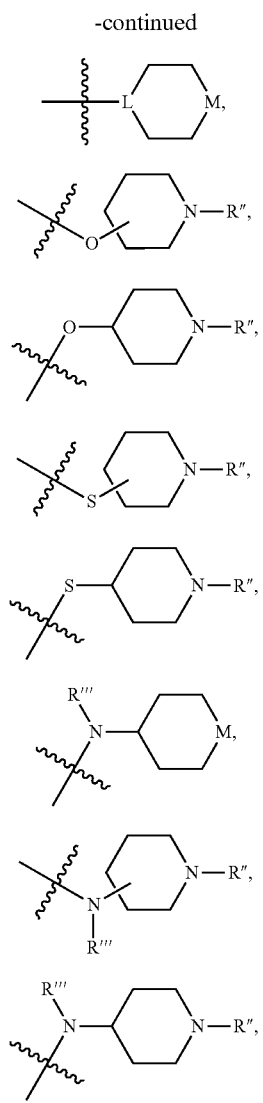

wherein
L is selected from the group consisting of CH and N;
M is selected from the group consisting of —CH(R")—, —CH$_2$—, —O—, —S—, —NH—, —N(—(CH$_2$)$_z$—R")—, —N(—(CH$_2$)$_z$—C(O)R")—, —N(—(CH$_2$)$_z$—C(O)OR")—, —N(—(CH$_2$)$_z$—S(O)$_2$R")—, —N(—(CH$_2$)$_z$—S(O)$_2$OR")— and —N(—(CH$_2$)$_z$—C(O)NR"R''')—, wherein z is an integer ranging from 0 to 6;
R" and R''' are each independently selected from: hydrogen; a C1-C10 alkyl group which is optionally substituted with one or more hetereoatoms such as halogen (selected from F, Cl, Br or I), oxygen, and nitrogen; a C1-C10 alkoxy group; an unsubstituted aryl, and an unsubstituted heteroaryl;
with the proviso that L and M are not both simultaneously CH and CH$_2$, respectively.

According to one embodiment, the "solubilising group" or "water-solubilising group" is selected from carboxylic acid, sulfonic acid, phosphoric acid, amine, quaternary ammonium group, heteroatom, heteroatomic groups as defined above, and structures (a)-(k) defined above.

Examples of solubilising groups are morpholinyl, piperidinyl, pyrrolidinyl, N—(C1-C6)alkyl piperidinyl, in particular N-methyl piperidinyl and N-ethyl piperidinyl, N-(4-piperidinyl)piperidinyl, 4-(1-piperidinyl)piperidinyl, 1-pyrrolidinylpiperidinyl, 4-morpholinopiperidinyl, 4-(N-methyl-1-piperazinyl)piperidinyl, piperazinyl, N—(C1-C6)alkylpiperazinyl, in particular N-methyl piperazinyl and N-ethyl piperazinyl, N—(C3-C6)cycloalkyl piperazinyl, in particular N-cyclohexyl piperazinyl, pyrrolidinyl, N—(C1-C6)alkyl pyrrolidinyl, in particular N-methyl pyrrolidinyl and N-ethyl pyrrolidinyl, diazepinyl, N—(C1-C6)alkyl azepinyl, in particular N-methyl azepinyl and N-ethyl azepinyl, homopiperazinyl, N-methyl homopiperazinyl, N-ethyl homopiperazinyl, imidazolyl.

The compounds of formula (I) may be used in the form of salts derived from pharmaceutically acceptable inorganic or organic acids. Unless otherwise indicated, "pharmaceutically acceptable salt" refers to a salt prepared by combining a compound of formula (I) with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts". Salts encompassed within the term "pharmaceutically acceptable salts" refer to non-toxic salts of the compounds of this invention which are generally prepared by reacting the free base with a suitable organic or inorganic acid. Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclic, carboxylic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, β-hydroxybutyrate, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate. Furthermore, where the compounds of the invention carry an acidic moiety, suitable pharmaceutically acceptable salts thereof may include alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts. Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl (CrCe) halides (e.g., methyl, ethyl, propyl, and butyl chlorides, bromides, and iodides), dialkyl sulfates (i.e., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others. Hemisalts of acids and bases may also be formed, for example, hemisulfate and hemicalcium salts.

Unless otherwise indicated, the language "compounds of formula (I)" includes all forms of the compound of the invention, including hydrates, solvates, isomers, crystalline and non-crystalline forms, isomorphs, polymorphs, and metabolites thereof. For example, the compounds of formula (I), or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm. Stereoisomers of the compounds of formula (I) include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Unless otherwise indicated, the language "compounds of formula (I)" include the tautomeric forms of compounds. Where structural isomers are interconvertible via a low energy barrier, tautomeric isomerism ('tautomerism') can occur. This can take the form of proton tautomerism in compounds of the invention containing, for example, an imino, keto, or oxime group, or so-called valence tautomerism in compounds which contain an aromatic moiety. It follows that a single compound may exhibit more than one type of isomerism. The various ratios of the tautomers in solid and liquid form is dependent on the various substituents on the molecule as well as the particular crystallization technique used to isolate a compound.

DETAILED DESCRIPTION

Compounds

The present invention relates to compounds of formula (I):

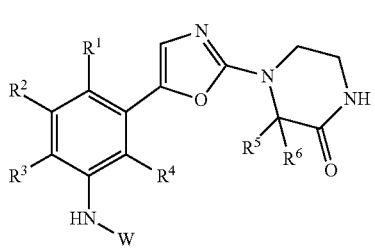

(I)

or a pharmaceutically acceptable salt thereof, wherein:
$R^1$, $R^2$, $R^3$ and $R^4$ are each independently selected from: hydrogen; cyano; haloalkyl (preferably $CF_3$); halogen (preferably F, Cl, Br or I); alkyl group optionally substituted with a group selected from an heterocycle and —NRR'; alkoxy group optionally substituted with a group selected from an heterocycle and —NRR'; water-solubilising group; heterocycle; —CO—NRR'; —SO$_2$—NRR'; —NRR'; —NR—CO—R'; and —NR—SO$_2$R' group; wherein R and R' are each independently selected from hydrogen and alkyl group;
$R^5$ is an alkyl group optionally substituted with a group selected from heterocycle, hydroxyl, cyano, amino and alkoxy;
$R^6$ is selected from hydrogen, alkyl group and cycloalkyl group;
W is selected from aryl and heteroaryl groups, the aryl or heteroaryl groups being optionally substituted by one or more (for example from one to four, such as one or two or three, for example one) substituents selected from: cyano; haloalkyl (preferably $CF_3$); halogen (preferably F, Cl, Br or I); an alkyl group optionally substituted with an heterocycle; a cycloalkyl group; an alkoxy group optionally substituted with an heterocycle; an aryl group; a heteroaryl group; a heterocycloalkyl group optionally substituted with an alkyl group; a water-solubilising group; —CO—NRR'; —SO$_2$—NRR'; —NRR'; —NR—CO—R'; and —NR—SO$_2$R' group; wherein R and R' are each independently selected from hydrogen and alkyl group.

According to one embodiment, $R^1$, $R^2$, $R^3$ and $R^4$ are each independently selected from the group consisting of hydrogen, halogen, an alkyl group optionally substituted with a heterocycle or —NRR', an alkoxy group optionally substituted with a heterocycle and a solubilising group; wherein R and R' are each independently selected from hydrogen and alkyl group.

According to one embodiment, at least three of $R^1$, $R^2$, $R^3$ and $R^4$ are hydrogen atoms. According to a specific embodiment, $R^1$, $R^3$ and $R^4$ are hydrogen atoms. According to another specific embodiment, $R^1$, $R^2$, $R^3$ and $R^4$ are all fourth hydrogen atoms. According to another specific embodiment, $R^3$ and $R^4$ are hydrogen, one of $R^1$ and $R^2$ is hydrogen and the other is selected from the group consisting of hydrogen, halogen, an alkyl group optionally substituted with a heterocycle or NRR' and an alkoxy group optionally substituted with a heterocycle.

According to a specific embodiment, $R^2$ is selected from hydrogen, halogen, alkyl group optionally substituted with a group selected from heterocycle and —NRR'; alkoxy group optionally substituted with a group selected from an heterocycle and NRR'. Preferably $R^2$ is selected from hydrogen, and alkyl group optionally substituted with a group selected from heterocycle and —NRR'; more preferably $R^2$ is selected from hydrogen, morpholin-4-ylmethyl, pyrrolidin-1-ylmethyl, dimethylaminomethyl.

According to a specific embodiment, $R^5$ is selected from alkyl group optionally substituted with hydroxyl. Preferably, $R^5$ is selected from methyl, ethyl, isopropyl, 2-hydroxyethyl. More preferably, $R^5$ is selected from methyl, ethyl, isopropyl.

According to a specific embodiment, $R^6$ is selected from hydrogen and alkyl group. Preferably, $R^6$ is selected from hydrogen and methyl.

According to a specific embodiment, $R^5$ is an optionally substituted alkyl group and $R^6$ is a hydrogen atom.

According to one embodiment, W is a substituted, preferably monosubstituted or disubstituted, heteroaryl or a substituted, preferably monosubstituted, aryl. According to one embodiment, W is a substituted heteroaryl, preferably W is a monosubstituted or disubstituted heteroaryl, more preferably W is as monosubstituted heteroaryl.

When W is a heteroaryl, the heteroaryl may be a 5-8 membered monocyclic ring. That ring may contain at least one nitrogen atoms, preferably one to three nitrogen atoms, more preferably one or two nitrogen atoms. According to a preferred embodiment, the heteroaryl is pyrimidine, preferably pyrimidin-2-yl. According to a preferred embodiment, W is 4-substituted pyrimidin-2-yl.

According to a specific embodiment, W is a 5-8 membered, monosubstituted or disubstituted, monocyclic ring containing at least one nitrogen atom.

According to a specific embodiment, each of the one or more substituents of W is independently selected from the group consisting of: cyano, $CF_3$, halogen, an alkyl group optionally substituted with a heterocycle, a cycloalkyl group, an alkoxy group optionally substituted with a heterocycle, an aryl group, a heteroaryl group, a heterocycloalkyl group optionally substituted with an alkyl group, and —NRR', wherein R and R' are each independently selected from hydrogen and alkyl group.

The present invention discloses compounds wherein each of the substituents of W may be independently selected from the group consisting of cyano, $CF_3$, halogen, an alkyl group optionally substituted with a heterocycle (such as an unsubstituted C1-C3 alkyl, for example methyl, ethyl, propyl), a cycloalkyl group (such as cyclopropyl), an alkoxy group optionally substituted with an heterocycle (such as methoxy), an aryl group (for example phenyl), an heteroaryl group (for example thiophene or pyridine), and an heterocycloalkyl group (for example morpholine, pyrrolidine or N-methylpiperazine).

In one embodiment, compounds of the invention of formula (I) are of formula (II):

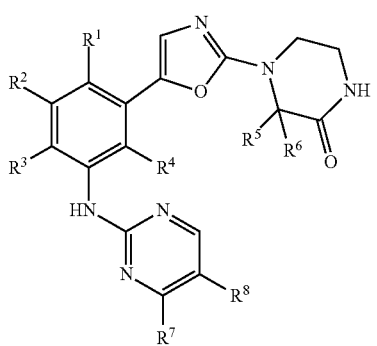

(II)

or a pharmaceutically acceptable salt thereof;
wherein $R^1$, $R^2$, $R^3$, $R^4$, $R^5$ and $R^6$ are as defined above, and $R^7$ and $R^8$ are each independently selected from: hydrogen; cyano; $CF_3$; halogen (preferably F, Cl, Br or I); an alkyl group optionally substituted with an heterocycle; a cycloalkyl group; an alkoxy group optionally substituted with an heterocycle; an aryl group; a heteroaryl group; a heterocycloalkyl group optionally substituted with an alkyl group; a water-solubilising group; and —NRR'; wherein R and R' are each independently selected from hydrogen and alkyl group.

According to one embodiment, in formula (II) at least three of $R^1$ to $R^4$ are hydrogen atoms, preferably each of $R^1$ to $R^4$ are hydrogen atoms. According to one embodiment, in formula (II), $R^5$ is an optionally substituted alkyl group and $R^6$ is hydrogen.

According to a specific embodiment, $R^7$ is selected from cyano, $CF_3$, an alkyl group, a cycloalkyl group, an alkoxy group, a heteroaryl group and heterocycloalkyl group optionally substituted with an alkyl group. Preferably $R^7$ is selected from cyano, $CF_3$, methyl, ethyl, isopropyl, cyclopropyl, methoxy, thiophenyl, morpholinyl, methylpiperazinyl, pyrrolidinyl.

According to a specific embodiment, $R^8$ is selected from hydrogen, and alkyl group. Preferably, $R^8$ is selected from hydrogen, methyl, ethyl, propyl, more preferably $R^8$ is a hydrogen atom.

In one embodiment, compounds of the invention of formula (I) are of formula (III):

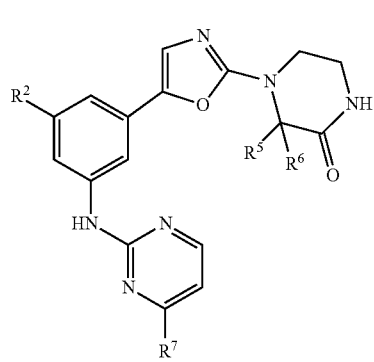

(III)

or a pharmaceutically acceptable salt thereof, wherein $R^2$, $R^5$, $R^6$ and $R^7$ are as defined above.

According to a specific embodiment, in compounds of formula (III), $R^2$ is an hydrogen or an alkyl group optionally substituted with an heterocycle. According to a more specific embodiment, $R^2$ is an hydrogen. According to another more specific embodiment, $R^2$ is an alkyl group substituted by:

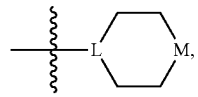

wherein L is selected from the group consisting of CH and N; and M is selected from the group consisting of —O— and —S— (for example morpholin-4-ylmethyl).

According to a specific embodiment, in compounds of formula (III), $R^5$ is an alkyl group such as an unsubstituted C1-C3 alkyl (for example methyl, ethyl or isopropyl). According to a more specific embodiment, $R^5$ is methyl, ethyl or isopropyl group. According to a preferred embodiment, $R^5$ is methyl group. According to another preferred embodiment, $R^5$ is ethyl group. According to another preferred embodiment, $R^5$ is isopropyl group.

According to a specific embodiment, in compounds of formula (III), $R^6$ is an hydrogen or an alkyl group such as methyl. According to a more specific embodiment, $R^6$ is an hydrogen. According to another more specific embodiment, $R^6$ is methyl group.

According to a specific embodiment, in compounds of formula (III), $R^7$ is:
cyano;
$CF_3$;
an alkyl group, such as an unsubstituted C1-C3 alkyl (for example methyl, ethyl or isopropyl);
a cycloalkyl group, such as an unsubstituted C3-C6 cycloalkyl (for example cyclopropyl);
an alkoxy group, such as an unsubstituted C1-C3 alkoxy (for example methoxy); or a heteroaryl group, such as an unsubstituted C3-C6 heteroaryl (for example thiophenyl).

According to a more specific embodiment, $R^7$ is methyl, ethyl or isopropyl group.

According to a preferred embodiment, $R^7$ is methyl group.

According to one embodiment, compounds of the invention are selected from:

3-Methyl-4-{5-[3-(4-methyl-pyrimidin-2-ylamino)-phenyl]-oxazol-2-yl}-piperazin-2-one;
3,3-Dimethyl-4-{5-[3-(4-methyl-pyrimidin-2-ylamino)-phenyl]-oxazol-2-yl}-piperazin-2-one;
3-Isopropyl-4-{5-[3-(4-methyl-pyrimidin-2-ylamino)-phenyl]-oxazol-2-yl}-piperazin-2-one;
4-{5-[3-(4-Ethyl-pyrimidin-2-ylamino)-phenyl]-oxazol-2-yl}-3-methyl-piperazin-2-one;
3,3-Dimethyl-4-{5-[3-(4-methyl-pyrimidin-2-ylamino)-5-morpholin-4-ylmethyl-phenyl]-oxazol-2-yl}-piperazin-2-one;
3-Methyl-4-{5-[3-(5-propyl-pyrimidin-2-ylamino)-phenyl]-oxazol-2-yl}-piperazin-2-one;
(R)-3-Methyl-4-{5-[3-(4-methyl-pyrimidin-2-ylamino)-phenyl]-oxazol-2-yl}-piperazin-2-one;
2-{3-[2-(2-Methyl-3-oxo-piperazin-1-yl)-oxazol-5-yl]-5-(morpholin-4-ylmethyl)-phenylamino}-pyrimidine-4-carbonitrile;
3-Methyl-4-{5-[3-((4-trifluoromethyl)-pyrimidin-2-ylamino)-phenyl]-oxazol-2-yl}-piperazin-2-one;
3-Methyl-4-{5-[3-(4-thiophen-2-yl-pyrimidin-2-ylamino)-phenyl]-oxazol-2-yl}-piperazin-2-one;
3-Ethyl-4-{5-[3-((4-trifluoromethyl)-pyrimidin-2-ylamino)-phenyl]-oxazol-2-yl}-piperazin-2-one;
3-Isopropyl-4-{5-[3-((4-trifluoromethyl)-pyrimidin-2-ylamino)-phenyl]-oxazol-2-yl}-piperazin-2-one;
4-{5-[3-(4-Methoxy-pyrimidin-2-ylamino)-phenyl]-oxazol-2-yl}-3-methyl-piperazin-2-one;
3-Methyl-4-{5-[3-(4-methyl-pyrimidin-2-ylamino)-5-morpholin-4-ylmethyl-phenyl]-oxazol-2-yl}-piperazin-2-one;
3-Methyl-4-{5-[3-morpholin-4-ylmethyl-5-((4-trifluoromethyl)-pyrimidin-2-ylamino)-phenyl]-oxazol-2-yl}-piperazin-2-one;
4-{5-[3-(5-Ethyl-pyrimidin-2-ylamino)-phenyl]-oxazol-2-yl}-3-methyl-piperazin-2-one;
2-{3-[2-(2-Methyl-3-oxo-piperazin-1-yl)-oxazol-5-yl]-phenylamino}-pyrimidine-4-carbonitrile;
3,3-Dimethyl-4-{5-[3-((4-trifluoromethyl)-pyrimidin-2-ylamino)-phenyl]-oxazol-2-yl}-piperazin-2-one;
(S)-3-Methyl-4-{5-[3-(4-methyl-pyrimidin-2-ylamino)-phenyl]-oxazol-2-yl}-piperazin-2-one;
3-Ethyl-4-{5-[3-(4-methyl-pyrimidin-2-ylamino)-phenyl]-oxazol-2-yl}-piperazin-2-one;
4-{5-[3-(4-Isopropyl-pyrimidin-2-ylamino)-phenyl]-oxazol-2-yl}-3-methyl-piperazin-2-one;
4-{5-[3-(4,5-Dimethyl-pyrimidin-2-ylamino)-phenyl]-oxazol-2-yl}-3,3-dimethyl-piperazin-2-one;
4-{5-[3-(4-Isopropyl-pyrimidin-2-ylamino)-phenyl]-oxazol-2-yl}-3,3-dimethyl-piperazin-2-one;
3-(2-Hydroxy-ethyl)-4-{5-[3-(4-methyl-pyrimidin-2-ylamino)-phenyl]-oxazol-2-yl}-piperazin-2-one;
3-Ethyl-4-{5-[3-(4-isopropyl-pyrimidin-2-ylamino)-phenyl]-oxazol-2-yl}-piperazin-2-one;
4-{5-[3-(4-Methoxy-pyrimidin-2-ylamino)-phenyl]-oxazol-2-yl}-3,3-dimethyl-piperazin-2-one;
3-Methyl-4-{5-[3-(4-morpholin-4-yl-pyrimidin-2-ylamino)-phenyl]-oxazol-2-yl}-piperazin-2-one;
3-Methyl-4-{5-[3-(4-pyrrolidin-1-yl-pyrimidin-2-ylamino)-phenyl]-oxazol-2-yl}-piperazin-2-one;
3-Methyl-4-(5-{3-[4-(4-methyl-piperazin-1-yl)-pyrimidin-2-yl amino]-phenyl}-oxazol-2-yl)-piperazin-2-one;
3,3-Dimethyl-4-{5-[3-(4-morpholin-4-yl-pyrimidin-2-ylamino)-phenyl]-oxazol-2-yl}-piperazin-2-one;
3,3-Dimethyl-4-(5-{3-[4-(4-methyl-piperazin-1-yl)-pyrimidin-2-ylamino]-phenyl}-oxazol-2-yl)-piperazin-2-one;
3,3-Dimethyl-4-{5-[3-(4-pyrrolidin-1-yl-pyrimidin-2-ylamino)-phenyl]-oxazol-2-yl}-piperazin-2-one;
3-Isopropyl-4-{5-[3-(4-morpholin-4-yl-pyrimidin-2-ylamino)-phenyl]-oxazol-2-yl}-piperazin-2-one;
3-Isopropyl-4-{5-[3-(4-pyrrolidin-1-yl-pyrimidin-2-ylamino)-phenyl]-oxazol-2-yl}-piperazin-2-one;
3-Isopropyl-4-(5-{3-[4-(4-methyl-piperazin-1-yl)-pyrimidin-2-ylamino]-phenyl}-oxazol-2-yl)-piperazin-2-one;
3-Isopropyl-4-{5-[3-(4-isopropyl-pyrimidin-2-ylamino)-phenyl]-oxazol-2-yl}-piperazin-2-one;
4-{5-[3-(4-Ethyl-pyrimidin-2-ylamino)-phenyl]-oxazol-2-yl}-3,3-dimethyl-piperazin-2-one;
4-{5-[3-(4-Ethyl-pyrimidin-2-ylamino)-phenyl]-oxazol-2-yl}-3-isopropyl-piperazin-2-one;
(S)-3-Isopropyl-4-{5-[3-(4-methyl-pyrimidin-2-ylamino)-phenyl]-oxazol-2-yl}-piperazin-2-one;
(R)-3-Isopropyl-4-{5-[3-(4-methyl-pyrimidin-2-ylamino)-phenyl]-oxazol-2-yl}-piperazin-2-one;
4-{5-[3-(4-Cyclopropyl-pyrimidin-2-ylamino)-phenyl]-oxazol-2-yl}-3-methyl-piperazin-2-one;
4-{5-[3-(4-Cyclopropyl-pyrimidin-2-ylamino)-phenyl]-oxazol-2-yl}-3,3-dimethyl-piperazin-2-one;
4-{5-[3-(4-Cyclopropyl-pyrimidin-2-ylamino)-phenyl]-oxazol-2-yl}-3-isopropyl-piperazin-2-one;
4-{5-[3-Dimethyl aminomethyl-5-(4-methyl-pyrimidin-2-ylamino)-phenyl]-oxazol-2-yl}-3,3-dimethyl-piperazin-2-one;
3,3-Dimethyl-4-{5-[3-(4-methyl-pyrimidin-2-ylamino)-5-pyrrolidin-1-ylmethyl-phenyl]-oxazol-2-yl}-piperazin-2-one;

and a pharmaceutically acceptable salt thereof.

Process of Manufacturing

The present invention further relates to processes of manufacturing of the compounds of the invention.

According to a first embodiment, the process of the invention comprises reacting a compound of formula (A):

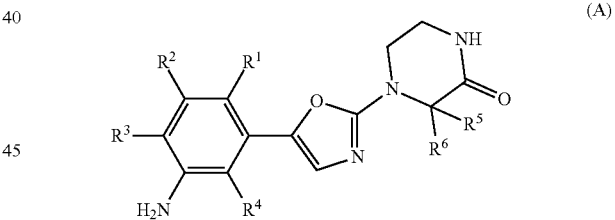

(A)

with a compound of formula W-X; wherein $R^1$, $R^2$, $R^3$, $R^4$, $R^5$, $R^6$, and W are as defined above and X represents a halogen atom; to afford a compound of formula (I) according to the invention, or a pharmaceutically acceptable salt thereof.

According to a second embodiment, the process of the invention comprises reacting a compound of formula (B):

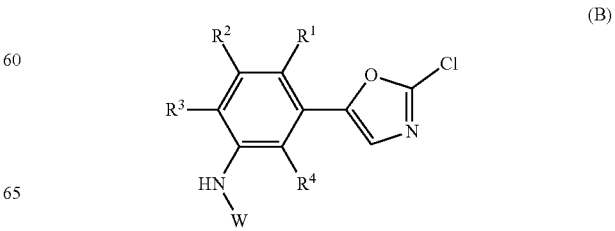

(B)

with a compound of formula (C):

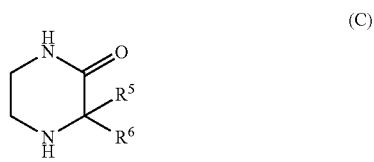

wherein $R^1$, $R^2$, $R^3$, $R^4$, $R^5$, $R^6$, and W are as defined above; to afford a compound of formula (I) according to the invention, or a pharmaceutically acceptable salt thereof.

Especially, compounds of the invention can be prepared by several methods including methods outlined in Schemes 1-4 below, wherein the substituents are as defined in formula (I) above, except where further noted. The synthetic methods described below are merely exemplary, and the compounds of the invention may be synthesized by alternate routes as appreciated by persons of ordinary skill in the art.

The non-commercial substituted piperazinones of formula (2) (Scheme 1) were prepared by reacting ethylene diamine with 2-bromo ester (1) using the method described by A. Benjahad et al (*Tetrahedron Lett.*, (1994), 35(51), 9545).

Scheme 1

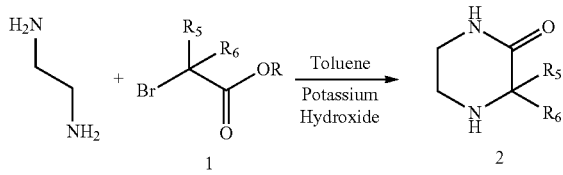

The piperazinones (2) may alternatively be prepared via N-Nosyaziridine (4) according to the protocol outlined in scheme 2. N-Nosyaziridine intermediate (4) is prepared from 2-chloroethylamine hydrochloride by first reacting with p-nitrosulfonyl chloride to give the N-Nosylamine (3) which is subsequently cyclised with potassium hydroxide to afford (4). Ring-opening with an amino acid methyl ester hydrochloride (5) gives the acyclic aminoester (6) which is cyclised in 2 steps: N-deprotection with thiophenol then heating to afford piperazinones (2).

Aromatic aldehydes (7) (Scheme 3 below) were reacted with p-toluenesulfonylmethyl isocyanide (TosMIC) to prepare the corresponding 5-arylsubstitued oxazoles (8) using the method of Van Leusen et. al. (*Tetrahedron Lett.*, (1972), 23, 2369). The non-commercial aldehydes (7) were prepared using literature methods. Deprotonation of the oxazole moiety (8) by a suitable organic base such as lithium hexamethyldisilazane (LiHMDS) and subsequent electrophilic chlorination was used to prepare the 2-chlorooxazole compounds (9). This allowed access to compounds (10) by substitution of the chlorine by substituted piperazinones (2). This substitution was performed either by heating in the presence of solvent such as isopropanol or under neat conditions. In certain cases and in the presence of solvent, compounds (10) can be obtained by using an acid such as HCl. Nitro compound (10) is reduced to form the corresponding aniline (11) (Intermediate (A)). Preferably, the reduction reaction is performed in the presence of hydrogen with a catalyst, such as a palladium on carbon 10 wt. %. Compounds (11) were used to prepare further analogues (12) of formula (1) by a direct nucleophilic displacement reaction in the presence of a suitable solvent such as alcohol and with heating in elevated temperature, where X of W-X can be F, I, Br or Cl. Presence of an acid such as HCl may or may not be necessary to drive the reaction to completion or to obtain improved yields. In certain cases compounds (12) can be obtained by using known metal-catalysed N-arylation protocols with a suitable combination of ligand and inorganic base.

Scheme 3

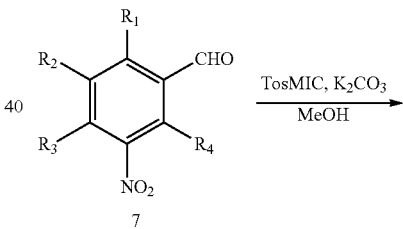

Scheme 2

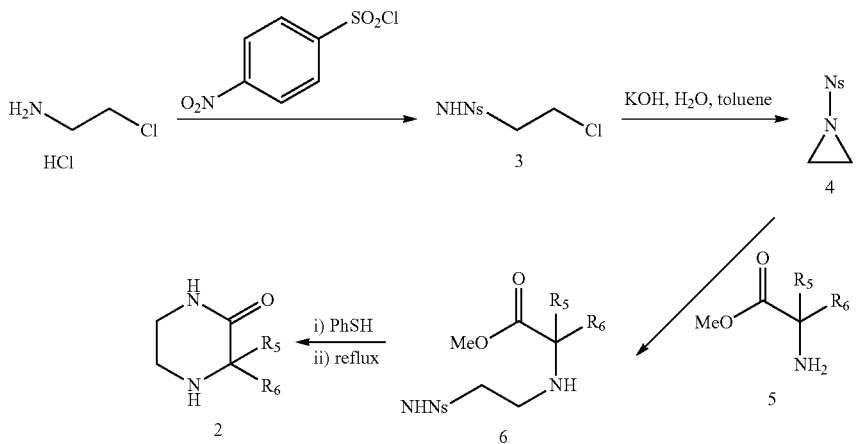

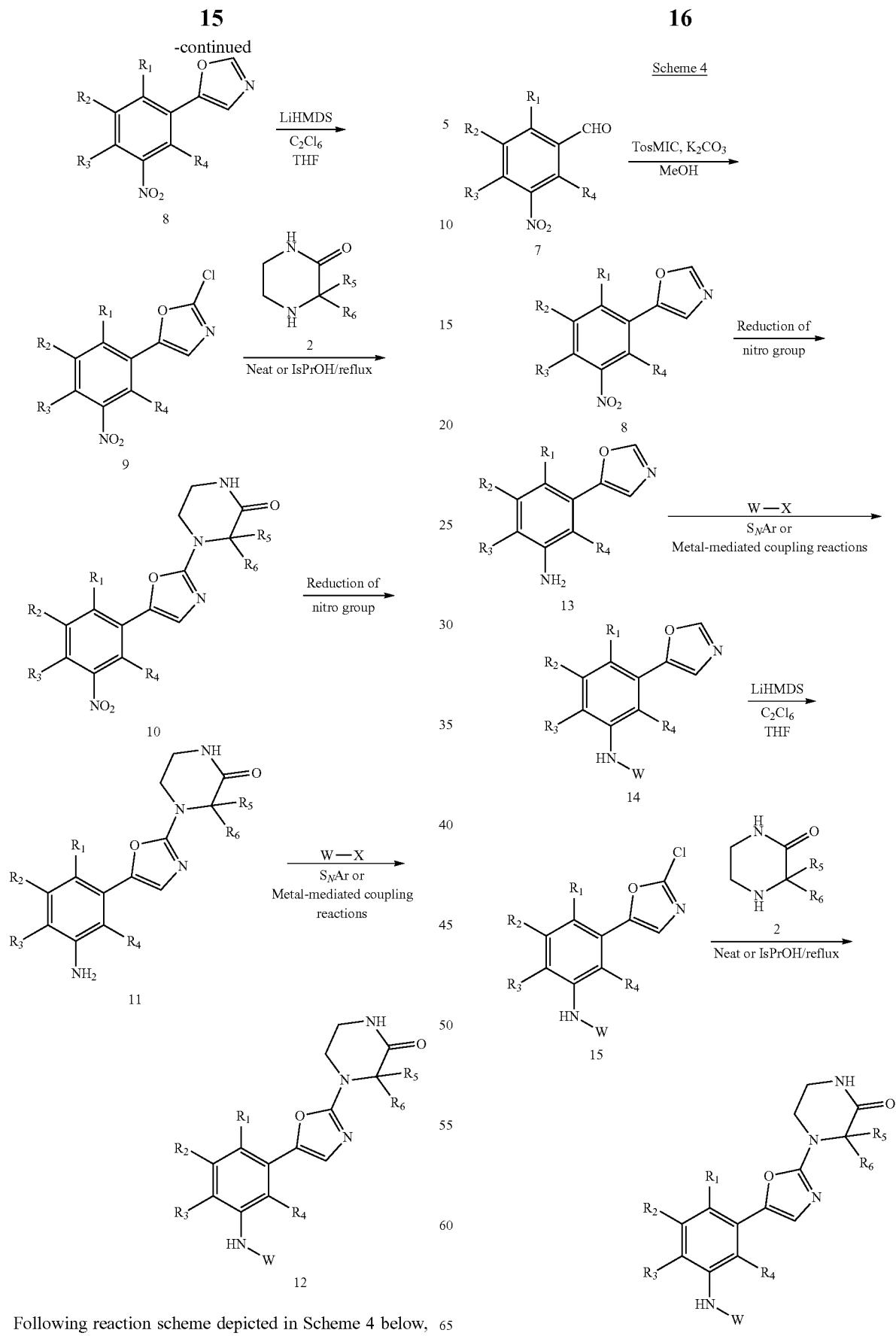
Following reaction scheme depicted in Scheme 4 below, compounds (12) of formula (I) were obtained by using the same protocols described above.

Pharmaceutical Composition

The present invention also relates to a pharmaceutical composition comprising a compound as described above. Accordingly, the present invention relates to a pharmaceutical composition comprising at least one compound of the invention, or a pharmaceutically acceptable salt thereof, and at least one pharmaceutically acceptable excipient and/or carrier.

According to one embodiment, the invention relates to a pharmaceutical composition comprising a compound of formula (I) as defined above, such as a compound of formula (II) or (III), or a pharmaceutically acceptable salt thereof, and at least one pharmaceutically acceptable excipient and/or carrier.

In the pharmaceutical composition of the invention, a compound of formula (I) may be the sole pharmaceutically active ingredient or it may be combined with one or more distinct pharmaceutically active ingredients. According to one embodiment, the pharmaceutical composition of the invention comprises a compound according to the invention, or a pharmaceutically acceptable salt thereof, as sole active pharmaceutical ingredient or in combination with another active pharmaceutical ingredient. According to one embodiment, the pharmaceutical composition of the invention comprises one compound of formula (I) as sole pharmaceutically active ingredient. According to another embodiment, the pharmaceutical composition of the invention comprises a compound of formula (I) in combination with one or more distinct pharmaceutically active ingredients.

Suitable carriers and excipients are widely known in the art and are commonly used for example to facilitate the processing of the active compounds into preparations which can be used pharmaceutically. Further details on techniques for formulation and administration may be found in the latest edition of Remington's Pharmaceutical Sciences (Maack Publishing Co., Easton, Pa.).

Various forms of excipients can be used depending on the desired mode of administration and some of them can improve or tailor the effectiveness of the active compound, e.g. by promoting a release profile rendering this active compound overall more effective for the treatment desired. The pharmaceutical compositions of the invention are suitable to be administered in various forms, for example in an injectable, pulverizable or ingestible form, for example via the intramuscular, intravenous, subcutaneous, intradermal, oral, topical, rectal, vaginal, ophthalmic, nasal, transdermal or parenteral route.

The pharmaceutical composition presently disclosed may be intended for oral administration. In this case, the composition may be formulated as tablets, pills, dragees, capsules, liquids, gels, syrups, slurries, suspensions, and the like, for ingestion by the patient.

The compositions presently disclosed may be a pharmaceutical or cosmetic composition. They may be intended for topical administration. Such compositions may be presented in the form of a gel, paste, ointment, cream, lotion, liquid suspension, aqueous-alcoholic or oily solutions, or dispersions of the lotion or serum type, or anhydrous or lipophilic gels, or emulsions of liquid or semi-solid consistency of the milk type, obtained by dispersing a fatty phase in an aqueous phase or vice versa, or of suspensions or emulsions of soft, semi-solid consistency of the cream or gel type, or alternatively of microemulsions, of microcapsules, of microparticles or of vesicular dispersions to the ionic and/or nonionic type. These compositions may be prepared according to standard methods.

The compositions presently defined may comprise any ingredient commonly used in dermatology and cosmetics. It may comprise at least one ingredient selected from hydrophilic or lipophilic gelling agents, hydrophilic or lipophilic active agents, preservatives, emollients, viscosity enhancing polymers, humectants, surfactants, preservatives, antioxidants, solvents, perfumes, fillers, screening agents, bactericides, odor absorbers and coloring matter. As oils which can be used in the invention, mineral oils (liquid paraffin), vegetable oils (liquid fraction of shea butter, sunflower oil), animal oils, synthetic oils, silicone oils (cyclomethicone) and fluorinated oils may be mentioned. Fatty alcohols, fatty acids (stearic acid) and waxes (paraffin, carnauba, beeswax) may also be used as fatty substances. Emulsifiers which can be used in the invention include, for example, glycerol stearate, polysorbate 60 and the PEG-6/PEG-32/glycol stearate mixture. Hydrophilic gelling agents which can be used in the invention include, for example, carboxyvinyl polymers (carbomer), acrylic copolymers such as acrylate/alkylacrylate copolymers, polyacrylamides, polysaccharides such as hydroxypropylcellulose, clays and natural gums. Lipophilic gelling agents which can be used in the invention include, for example modified clays such as bentones, metal salts of fatty acids such as aluminum stearates and hydrophobic silica, or alternatively ethylcellulose and polyethylene. As hydrophilic active agents, proteins or protein hydrolysates, amino acids, polyols, urea, allantoin, sugars and sugar derivatives, vitamins, starch and plant extracts, in particular those of Aloe Vera may be used. As lipophilic active agents, retinol (vitamin A) and its derivatives, tocopherol (vitamin E) and its derivatives, essential fatty acids, ceramides and essential oils may be used. These agents add extra moisturizing or skin softening features when utilized. In addition, a surfactant can be included in the composition so as to provide deeper penetration of the compound capable of depleting mast cells, such as a tyrosine kinase inhibitor. Among the contemplated ingredients, one may chose penetration enhancing agents selected for example from the group consisting of mineral oil, water, ethanol, triacetin, glycerin and propylene glycol; cohesion agents selected for example from the group consisting of polyisobutylene, polyvinyl acetate and polyvinyl alcohol, and thickening agents. Chemical methods of enhancing topical absorption of drugs are well known in the art. For example, compounds with penetration enhancing properties include sodium lauryl sulfate (Dugard, P. H. and Sheuplein, R. J., "Effects of Ionic Surfactants on the Permeability of Human Epidermis: An Electrometric Study", *J. Ivest. Derniatol.*, V.60, (1973), pp. 263-69), lauryl amine oxide (Johnson et al, U.S. Pat. No. 4,411,893), azone (Rajadhyaksha, U.S. Pat. Nos. 4,405,616 and 3,989,816) and decylmethyl sulfoxide (Sekura, D. L. and Scala, J., "The Percutaneous Absorption of Alkylmethyl Sulfides", Pharmacology of the Skin, Advances In Biology of Skin, (Appleton-Century Craft) V. 12, (1972), pp. 257-69). It has been observed that increasing the polarity of the head group in amphoteric molecules increases their penetration-enhancing properties but at the expense of increasing their skin irritating properties (Cooper, E. R. and Berner, B., "Interaction of Surfactants with Epidermal Tissues: Physiochemical Aspects", Surfactant Science Series, V. 16, Reiger, M. M. ed. (Marcel Dekker, Inc.), (1987), pp. 195-210). Chemical enhancers may also be co-solvents. These materials are absorbed topically relatively easily, and, by a variety of mechanisms, achieve permeation enhancement for some drugs. Ethanol (Gale et al, U.S. Pat. No. 4,615,699 and Campbell et al., U.S. Pat. Nos. 4,460,372 and 4,379,454), dimethyl sulfoxide (U.S. Pat. Nos. 3,740,420 and 3,743,727, and 4,575,515), and glycerin derivatives (U.S. Pat. No. 4,322,433) are a few examples of compounds which have shown an ability to enhance the absorption of various compounds.

The pharmaceutical compositions presently disclosed can also be intended for administration with aerosolized formulation to target areas of a patient's respiratory tract. Devices and methodologies for delivering aerosolized bursts of a formulation of a drug is disclosed in U.S. Pat. No. 5,906, 202. Formulations are preferably solutions, e.g. aqueous solutions, ethanolic solutions, aqueous/ethanolic solutions, saline solutions, colloidal suspensions and microcrystaline suspensions. For example, aerosolized particles comprise the active ingredient mentioned above and a carrier, (e.g., a pharmaceutically active respiratory drug and carrier) which are formed upon forcing the formulation through a nozzle which nozzle is preferably in the form of a flexible porous membrane. The particles have a size which is sufficiently small such that when the particles are formed they remain suspended in the air for a sufficient amount of time such that the patient can inhale the particles into the patient's lungs. Suitable devices for the administration of the present compounds to a patient's respiratory tract are discussed for example in U.S. Pat. No. 5,556,611:

liquid gas systems (a liquefied gas is used as propellant gas e.g. low-boiling FCHC or propane, butane in a pressure container);

suspension aerosol (the active substance particles are suspended in solid form in the liquid propellant phase);

pressurized gas system (a compressed gas such as nitrogen, carbon dioxide, dinitrogen monoxide, or air is used.

Thus, the pharmaceutical composition presently disclosed is made in that the active substance is dissolved or dispersed in a suitable nontoxic medium and said solution or dispersion atomized to an aerosol, i.e. distributed extremely finely in a carrier gas. This is technically possible for example in the form of aerosol propellant gas packs, pump aerosols or other devices known per se for liquid misting and solid atomizing which in particular permit an exact individual dosage. Therefore, to the present invention also discloses aerosol devices comprising a compound as defined above and such a formulation, preferably with metered dose valves.

The pharmaceutical compositions presently disclosed can also be intended for intranasal administration. In this regard, pharmaceutically acceptable carriers for administering the compound to the nasal mucosal surfaces will be readily appreciated by the ordinary artisan. These carriers are described in the "Remington's Pharmaceutical Sciences" 16$^{th}$ edition, (1980), Ed. By Arthur Osol.

For administration via the upper respiratory tract, the composition can be formulated into a solution, e.g., water or isotonic saline, buffered or unbuffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2 (Remington's, Id. at page 1445). Of course, the ordinary artisan can readily determine a suitable saline content and pH for an innocuous aqueous carrier for nasal and/or upper respiratory administration. Common intranasal carriers include nasal gels, creams, pastes or ointments with a viscosity of, e.g., from about 10 to about 3000 cps, or from about 2500 to 6500 cps, or greater, may also be used to provide a more sustained contact with the nasal mucosal surfaces. Such carrier viscous formulations may be based upon, simply by way of example, alkylcelluloses and/or other biocompatible carriers of high viscosity well known to the art (see e.g., Remington's, cited supra. A preferred alkylcellulose is, e.g., methylcellulose in a concentration ranging from about 5 to about 1000 or more mg per 100 ml of carrier. A more preferred concentration of methyl cellulose is, simply by way of example, from about 25 to about 150 mg per 100 ml of carrier. Other ingredients, such as known preservatives, colorants, lubricating or viscous mineral or vegetable oils, perfumes, natural or synthetic plant extracts such as aromatic oils, and humectants and viscosity enhancers such as, e.g., glycerol, can also be included to provide additional viscosity, moisture retention and a pleasant texture and odor for the formulation. For nasal administration of solutions or suspensions, various devices are available in the art for the generation of drops, droplets and sprays.

A premeasured unit dosage dispenser including a dropper or spray device containing a solution or suspension for delivery as drops or as a spray is prepared containing one or more doses of the drug to be administered. Also disclosed is a kit containing one or more unit dehydrated doses of a compound of formula (I) as presently disclosed, together with any required salts and/or buffer agents, preservatives, colorants and the like, ready for preparation of a solution or suspension by the addition of a suitable amount of water.

Medical Use

The present invention further relates to the use of a compounds according to the invention as a medicament. According to one embodiment, the invention relates to a compound according to the invention, or a pharmaceutically acceptable salt thereof, for use as a medicament. Especially, the present invention is directed to a compound of formula (I) as defined above, such as a compound of formula (II) or (III), or a pharmaceutically acceptable salt thereof, for use as a medicament.

The compounds of formula (I) or pharmaceutically salts thereof as presently disclosed (also jointly referred to as "compounds of formula (I)") are endowed with Syk tyrosine kinase inhibiting activity. In particular, they may inhibit (thereby regulating) the signal transduction mediated by Syk.

Accordingly, in one aspect the present invention discloses a method for treating a disease or disorder associated with unregulated tyrosine kinase activity, especially unregulated Syk activity, said method comprising administering an effective amount of a compound of formula (I) to a subject (such as a human or animal subject) in need of such treatment.

According to one embodiment, the invention relates to a compound of the invention, or a pharmaceutically acceptable salt thereof, for use in treating a disease or disorder associated with unregulated tyrosine kinase activity, especially, unregulated Syk activity.

According to one embodiment, the invention relates to the use of a compound of the invention, or a pharmaceutically acceptable salt thereof, for the manufacturing of a medicament for treating a disease or disorder associated with unregulated tyrosine kinase activity, especially, unregulated Syk activity.

Effective amounts of the compounds of formula (I) are generally comprised between 0.1 mg and 2 g of the compound per day and per kilogram of body weight.

In another aspect, the present invention discloses a method for modulating, regulating, and/or inhibiting, in cells, the signal transduction mediated by Syk protein kinase. Said method comprises administering to cells at least one compound of formula (I) as defined above, such as a compound of formula (II) or (III), or a pharmaceutically acceptable salt thereof.

The present invention discloses the use of at least one compound of formula (I) or a pharmaceutically acceptable salt thereof, for the in vitro or in vivo selective inhibition of Syk.

The methods presently disclosed may be for treating a hematological, an inflammatory, an autoimmune, a proliferative, a metabolic, an allergic and/or degenerative disease or disorder in a patient.

In one embodiment, said subject or patient has been diagnosed as having hematological disorders, allergic disorders, metabolic disorders, inflammatory disorders, autoimmune disorders, degenerative disease and/or proliferative disorders.

Diseases and disorders known to be associated with unregulated signal transduction mediated by Syk are, for example:

hematological disorders such as Non-Hodgkin Lymphoma and leukemia including Diffuse large B-cell lymphoma (DLBCL) Follicular lymphoma (FL), Mantle cell lymphoma (MCL), B-cell chronic lymphocytic leukemia (B-CLL)/small lymphocytic lymphoma (SLL), Waldenstrom's macroglbulinemia (WM), Marginal zone lymphoma (MZL), Burkitt lymphoma and peripheral T-cell lymphomas (PTCL), as well as multiple myeloma (MM), myelodysplatic syndrome (MDS), myelodysplasia with myelofibrosis;

proliferative disorders or neoplastic diseases such as mastocytosis, solid tumours including head and neck cancer, hepatocellular carcinoma, and human gastrointestinal disorders;

metabolic diseases such diabetes mellitus and its chronic complications, obesity, diabetes type II, hyperlipidemias and dyslipidemias, atherosclerosis; hypertension and cardiovascular disease;

allergic diseases such as asthma, allergic rhinitis, allergic sinusitis, anaphylactic syndrome, urticaria, angioedema, atopic dermatitis, allergic contact dermatitis, erythema nodosum, erythema multiforme, cutaneous necrotizing venulitis and insect bite skin inflammation and blood sucking parasitic infestation;

bone resorption (osteoporosis);

angiogenesis;

inflammatory diseases such as rheumatoid arthritis, conjunctivitis, rheumatoid spondylitis, osteoarthritis, gouty arthritis and other arthritic conditions;

autoimmune diseases such as multiple sclerosis, psoriasis, intestine inflammatory disease, ulcerative colitis, Crohn's disease, rheumatoid arthritis and polyarthritis, local and systemic scleroderma, systemic lupus erythematosus, discoid lupus erythematosus, cutaneous lupus, dermatomyositis, polymyositis, Sjogren's syndrome, nodular panarteritis, autoimmune enteropathy, as well as proliferative glomerulonephritis and T-cell mediated autoimmune diabetes;

graft-versus-host disease or graft rejection for allogeneic hematopoietic cell transplantation for the treatment of leukemia and lymphoma, cardiac allograft and in any organ transplantation such as kidney, pancreas, liver, and lung;

Other autoimmune diseases embraced by the invention include active chronic hepatitis and chronic fatigue syndrome;

vasculitis;

viral infection;

fungal infection;

bacterial infection;

CNS disorders such as Nasu-Hakola disease, psychiatric disorders, migraine, pain, memory loss and nerve cells degeneracy. More particularly, the method according to the invention is useful for the treatment of the following disorders: depression including dysthymic disorder, cyclothymic disorder, bipolar depression, severe or "melancholic" depression, atypical depression, refractory depression, seasonal depression, anorexia, bulimia, premenstrual syndrome, post-menopause syndrome, other syndromes such as mental slowing and loss of concentration, pessimistic worry, agitation, self-deprecation, decreased libido, pain including, acute pain, postoperative pain, chronic pain, nociceptive pain, cancer pain, neuropathic pain, psychogenic pain syndromes, anxiety disorders including anxiety associated with hyperventilation and cardiac arrhythmias, phobic disorders, obsessive-compulsive disorder, post-traumatic stress disorder, acute stress disorder, generalized anxiety disorder, psychiatric emergencies such as panic attacks, including psychosis, delusional disorders, conversion disorders, phobias, mania, delirium, dissociative episodes including dissociative amnesia, dissociative fugue and dissociative identity disorder, depersonalization, catatonia, seizures, severe psychiatric emergencies including suicidal behaviour, self-neglect, violent or aggressive behaviour, trauma, borderline personality, and acute psychosis, schizophrenia including paranoid schizophrenia, disorganized schizophrenia, catatonic schizophrenia, and undifferentiated schizophrenia;

neurodegenerative diseases including Alzheimer's disease, Parkinson's disease, Huntington's disease, the prion diseases, Motor Neurone Disease (MND), and Amyotrophic Lateral Sclerosis (ALS);

Cerebral ischemia;

Retinal ischemia;

Ischemic stroke;

Fibrosis.

Hematological malignancies may be non-Hodgkin lymphoma (NHL) including B-CLL/SLL, DLBCL, FL, MCL and WM, peripheral T-cell lymphoma and myelodysplastic syndromes (MDS). Proliferative disorder may be cancer. Autoimmune disorders may be multiple sclerosis, psoriasis, intestine inflammatory disease, ulcerative colitis, Crohn's disease, rheumatoid arthritis and polyarthritis, local and systemic scleroderma, systemic lupus erythematosus, discoid lupus erythematosus, cutaneous lupus, dermatomyositis, polymyositis, Sjogren's syndrome, nodular panarteritis, autoimmune enteropathy, atopic dermatitis and/or proliferative glomerulonephritis. Metabolic diseases may be diabetes mellitus and its chronic complications, obesity, diabetes type II, hyperlipidemias and dyslipidemias, atherosclerosis; hypertension and cardiovascular disease. Inflammatory diseases may be rheumatoid arthritis, conjunctivitis, rheumatoid spondylitis, osteoarthritis, gouty arthritis and other arthritic conditions. Allergic diseases may be asthma, allergic rhinitis, allergic sinusitis, anaphylactic syndrome, urticaria, angioedema, atopic dermatitis, allergic contact dermatitis, erythema nodosum, erythema multiforme, cutaneous necrotizing venulitis and insect bite skin inflammation and/or blood sucking parasitic infestation. Neurologic diseases may be Huntington's disease, schizophrenia, Parkinson's disease and/or Alzheimer's disease.

Accordingly, the invention also relates to a compound of the invention, or a pharmaceutically acceptable salt thereof, for use in the treatment of a disease or disorder selected from the group consisting of hematological disorders, proliferative disorders, autoimmune disorders, metabolic disorders, inflammatory diseases, allergic diseases and/or neurological diseases. Especially, a compound of formula (I), such as a compound of formula (II) or (III), or a pharmaceutically acceptable salt thereof may be used for treating a disease or disorder disclosed above such as hematological disorders, proliferative disorders, autoimmune disorders, metabolic disorders, inflammatory disorders, allergic diseases and/or neurological diseases.

According to one embodiment, the invention also relates to the use of a compound of the invention, or a pharmaceutically acceptable salt thereof, for the manufacturing of a medicament for treating a disease or disorder selected from the group consisting of hematological disorders, proliferative disorders, autoimmune disorders, metabolic disorders, inflammatory diseases, allergic diseases and/or neurological diseases.

In the methods presently disclosed, the compound of formula (I) or a pharmaceutically acceptable salt thereof, may be used as sole active pharmaceutical ingredient or in combination with another active pharmaceutical ingredient.

The present invention discloses a method for preventing or treating a disease or disorder selected form hematological disorders, proliferative disorders, metabolic disorders, inflammatory disorders, autoimmune disorders, allergic diseases and neurological diseases, that method comprising simultaneously or sequentially administering to a human or animal subject in need thereof at least one compound of formula (I) or a pharmaceutically acceptable salt thereof in combination with another active pharmaceutical ingredient, in sufficient amounts to provide a therapeutic effect.

According to one embodiment, the invention relates to a pharmaceutical composition as described above, comprising a compound according to the invention, or a pharmaceutically acceptable salt thereof, and another active pharmaceutical ingredient as a combined preparation for sequential, simultaneous or separate use in the treatment of a disease or disorder selected from the group consisting of hematological disorders, proliferative disorders, autoimmune disorders, metabolic disorders, inflammatory diseases, allergic diseases and neurological diseases.

The present invention discloses a pharmaceutical composition comprising a compound of formula (I) such as a compound of formula (II) or (III), or a pharmaceutically acceptable salt thereof, and another active pharmaceutical agent as a combined preparation for sequential, simultaneous or separate use in the treatment of a disease or disorder selected from the group consisting of hematological disorders, proliferative disorders, autoimmune disorders, inflammatory disorders, allergic diseases and/or neurological diseases.

The present invention discloses the use of a compound of formula (I) such as a compound of formula (II) or (III), or a pharmaceutically acceptable salt thereof optionally in combination with another pharmaceutically active agent, for the manufacture of a medicament for the treatment of a a disease or disorder selected from the group consisting of a hematological disorder, a proliferative disorder, a metabolic disorder, an autoimmune disorder, an inflammatory disorder, an allergic disorder and a neurological disease.

Although methods and uses disclosed above refer to a compound of formula (I), such as a compound of formula (II) or (III), or a pharmaceutically acceptable salt thereof, whenever technically compatible they are to be understood to equally refer to pharmaceutical compositions including the same compounds.

EXAMPLES

The invention is now illustrated by Examples which represent currently preferred embodiments which make up a part of the invention, but which in no way are to be used to limit the scope of it.

Chemistry—Synthesis of the Compounds of the Invention

The invention will be more fully understood by reference to the following preparative examples, but they should not be construed as limiting the scope of the invention.

Material and Methods

All chemicals used were commercial reagent grade products. Solvents were of anhydrous commercial grade and were used without further purification. THF was freshly distilled under a stream of argon before use. The progress of the reactions was monitored by thin layer chromatography using precoated silica gel 60F 254, Merck TLC plates, which were visualized under UV light. Multiplicities in $^1$H NMR spectra are indicated as singlet (s), broad singlet (br s), doublet (d), triplet (t), quadruplet (q), and multiplet (m) and the NMR spectrum were performed either on a Bruker 300 or 400 MHz spectrometer. Enantiomeric purity of chiral compounds (expressed as a % enantiomeric excess, % e.e.) was determined by isocratic UPLC on a Chiralpak IC chiral column 5 μm, 4.6×250 mm eluting with 1:1 heptane/ethanol (vol/vol) at a flow rate of 0.8 ml/min.

Abbreviations

CDCl$_3$ Deuterochloroform;
Conc. HCl Concentrated hydrochloric acid (37%);
DCM Dichloromethane;
DMSO-d$_6$ Hexadeuterodimethyl sulfoxide;
EtOAc Ethyl acetate;
EtOH Ethanol;
Fe(acac)$_3$ Tris(acetylacetonato) iron(III);
h Hour(s);
LiHMDS Lithium bis(trimethylsilyl)amide;
Mins Minutes;
Pd(PPh$_3$)$_4$ Tetrakis(triphenylphosphine)palladium(0);
RT Room temperature;
SiO$_2$ Silica gel;
TosMIC p-Toluenesulfonylmethyl isocyanide;
THE Tetrahydrofuran;
r.t. Retention time.

Synthesis of Compound 001

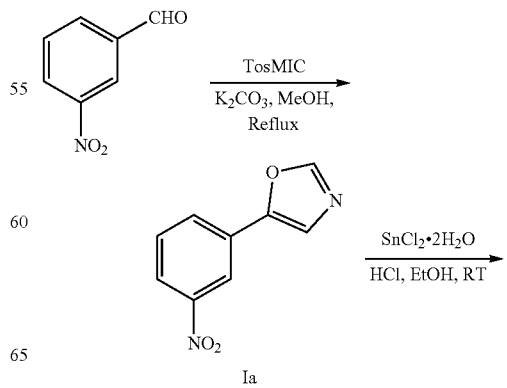

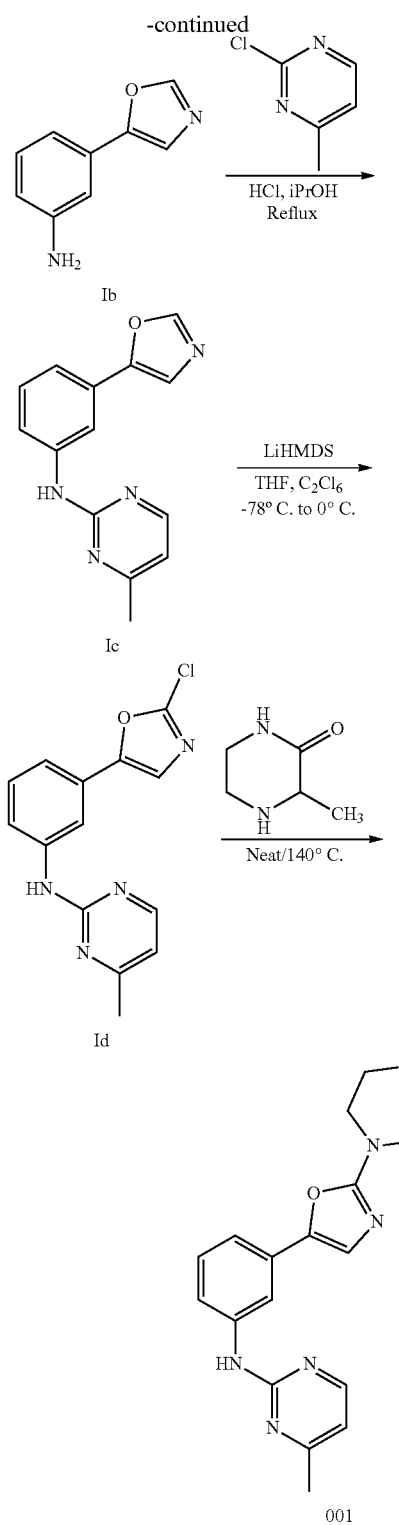

Preparation of 5-(3-Nitro-phenyl)-oxazole (Ia)

A solution of 3-nitrobenzaldehyde (15.0 g, 99.3 mmol) in methanol (400 ml) was treated with TosMIC (21.3 g, 109 mmol) and $K_2CO_3$ (16.5 g, 119 mmol) and heated to reflux for 30 mins. The cooled solution was concentrated and treated with water (400 ml) to form copious precipitate and was filtered. The filter cake was washed with water, then the solid was taken up in EtOAc and dried over $MgSO_4$. The solution was filtered and evaporated and the resultant solid was dried under vacuum to give the title compound as a beige solid (18.0 g, 95%). $^1$H NMR (400 MHz, DMSO-$d_6$) δ 8.56 (s, 1H), 8.50 (t, J=1.9 Hz, 1H), 8.21 (ddd, J=8.2, 2.3, 1.0 Hz, 1H), 8.17 (ddd, J=7.8, 1.6, 1.0 Hz, 1H), 7.99 (s, 1H), 7.78 (t, J=8.0 Hz, 1H).

Preparation of 3-Oxazol-5-yl-phenylamine (Ib)

A solution of intermediate Oa (3.52 g, 18.5 mmol) in absolute ethanol (210 ml) was treated with water (21 ml) then $SnCl_2.2H_2O$ (20.9 g, 92.6 mmol) and conc. HCl (15 ml, 180 mmol). After stirring at room temperature overnight, the solution was taken to pH 8 with 10% aqueous NaOH solution and extracted repeatedly with EtOAc. The organics were dried ($MgSO_4$), filtered and evaporated to afford the title compound as a pale orange powder (2.74 g, 93%). $^1$H NMR (400 MHz, DMSO-$d_6$) δ 8.37 (s, 1H), 7.49 (s, 1H), 7.10 (t, J=7.8 Hz, 1H), 6.90 (t, J=1.8 Hz, 1H), 6.86 (d, J=7.6 Hz, 1H), 6.59-6.54 (m, 1H), 5.25 (s, 2H).

Preparation of (4-Methyl-pyrimidin-2-yl)-(3-oxazol-5-yl-phenyl)-amine (Ic)

A solution of intermediate Ib (1.00 g, 6.24 mmol) in 2-propanol (50 ml) was treated with 2-chloro-4-methylpyrimidine (800 mg, 6.24 mmol) and 1.25M HCl solution in ethanol (7.5 ml, 9.38 mmol) and heated to reflux overnight. The solvent was evaporated and the residue treated with water and extracted with EtOAc. The organics were dried ($MgSO_4$), filtered and evaporated to afford the title compound as a beige solid (1.04 g, 66%). $^1$H NMR (400 MHz, DMSO-$d_6$) δ 9.71 (s, 1H), 8.45 (s, 1H), 8.37 (d, J=4.9 Hz, 1H), 8.23 (s, 1H), 7.76 (d, J=7.9 Hz, 1H), 7.60 (s, 1H), 7.37 (t, J=7.8 Hz, 1H), 7.30 (d, J=7.5 Hz, 1H), 6.77 (d, J=4.9 Hz, 1H), 2.38 (s, 3H).

Preparation of [3-(2-Chloro-oxazol-5-yl)-phenyl]-(4-methyl-pyrimidin-2-yl)-amine (Id)

A solution of intermediate Ic (1.23 g, 4.88 mmol) in dry THF (60 ml) under argon at −78° C. was treated with 1M LiHMDS solution in THF (7.20 mmol, 7.20 mmol) dropwise. After 45 mins at −78° C., hexachloroethane (1.39 g, 5.87 mmol) was added in one portion and stirring continued for a further 40 mins before warming to RT. The solution was then cooled to −78° C. once more, treated with 1M LiHMDS (7.20 ml, 7.20 mmol) dropwise and immediately allowed to warm to room temperature. The solution was treated with water and extracted with EtOAc. The combined organics were washed with brine, dried ($MgSO_4$), filtered and evaporated. The residue was purified by column chromatography ($SiO_2$, 20% to 30% EtOAc in cyclohexane) to afford the title compound as a pale yellow solid (1.17 g, 84%). $^1$H NMR (400 MHz, DMSO-$d_6$) δ 9.74 (s, 1H), 8.37 (d, J=5.0 Hz, 1H), 8.19 (t, J=1.8 Hz, 1H), 7.79 (dd, J=8.0, 1.8 Hz, 1H), 7.70 (s, 1H), 7.38 (t, J=7.9 Hz, 1H), 7.27 (d, J=7.7 Hz, 1H), 6.78 (d, J=5.0 Hz, 1H), 2.38 (s, 3H).

Preparation of 3-Methyl-4-[5-[3-(4-methyl-pyrimidin-2-ylamino)-phenyl]-oxazol-2-yl]-piperazin-2-one (Compound 001)

A mixture of intermediate Id (500 mg, 1.74 mmol) and 3-methyl-2-piperazinone (500 mg, 4.35 mmol) was heated to 140° C. for 30 mins. The cooled solid residue was taken up in a little hot ethanol, treated with $NaHCO_3$ solution (sat aqu) and extracted with EtOAc. The combined organics were dried ($MgSO_4$), filtered and evaporated to afford a yellow semi-solid consisting of the product with significant impurities. The solid was washed with EtOAc to afford the title compound as a white solid (265 mg, 42%). Further precipitate was isolated by filtration of the aqueous phase to afford a second crop (160 mg, 25%). $^1$H NMR (400 MHz, DMSO-$d_6$) δ 9.56 (s, 1H), 8.34 (d, J=5.0 Hz, 1H), 8.10 (t, J=1.8 Hz, 1H), 8.07 (d, J=2.5 Hz, 1H), 7.63 (dd, J=8.1, 1.2 Hz, 1H), 7.26 (dd, J=13.0, 5.0 Hz, 2H), 7.13 (d, J=7.9 Hz, 1H), 6.75 (d, J=5.0 Hz, 1H), 4.40 (q, J=6.9 Hz, 1H), 3.94 (dt, J=13.0, 3.6 Hz, 1H), 3.56-3.48 (m, 1H), 3.40 (tdd, J=9.8, 4.0, 1.0 Hz, 1H), 3.30-3.23 (m, 1H), 2.38 (s, 3H), 1.44 (d, J=7.0 Hz, 3H).

Synthesis of Compound 002

Preparation of 2-Chloro-5-(3-nitro-phenyl)-oxazole (IIb)

Prepared as for Intermediate Id above from Intermediate Ia followed by purification by column chromatography (SiO$_2$, 20% EtOAc in cyclohexane) to afford the title compound as a pale yellow solid (4.54 g, 77%). $^1$H NMR (400 MHz, CDCl$_3$) δ 8.45-8.43 (m, 1H), 8.21 (ddd, J=8.2, 2.2, 0.9 Hz, 1H), 7.91 (ddd, J=7.8, 1.5, 1.0 Hz, 1H), 7.64 (t, J=8.0 Hz, 1H), 7.46 (s, 1H).

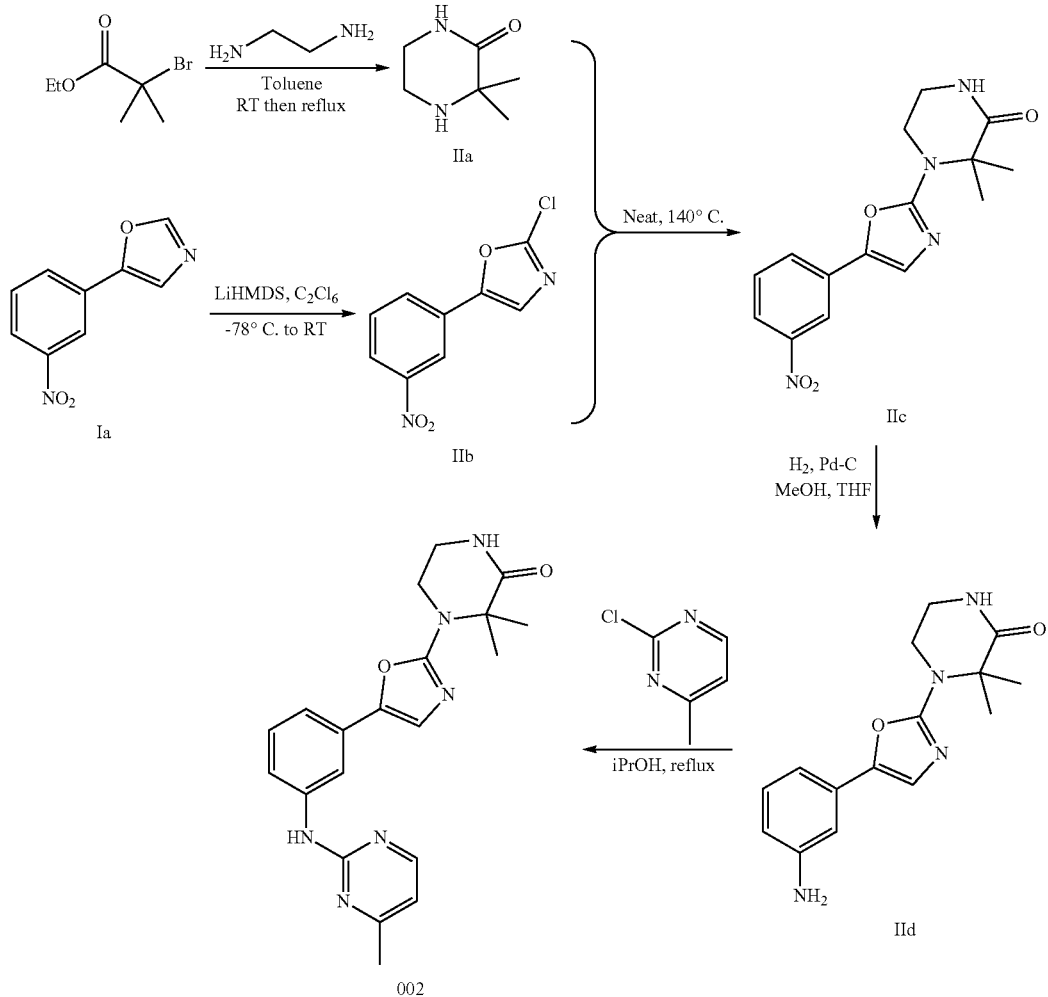

Preparation of 3,3-Dimethyl-piperazin-2-one (IIa)

A solution of ethylenediamine (25.6 ml, 383 mmol) in toluene (40 ml) was treated with a solution of ethyl 2-bromoisobutyrate (9.54 ml, 65.1 mmol) in toluene (40 ml) dropwise over 3 h. The mixture was then heated to reflux for 4 h, and once cooled, treated with a solution of KOH (3.46 g, mmol) in ethanol (45 ml). Once around 50% of the solvent had been removed under vacuum, a white inorganic precipitate was removed by filtration and the filtrate evaporated thoroughly to give an orange solid. This solid was recrystallised from a minimum of acetone after standing at 4° C. to afford the title compound as a white crystalline solid (3.86 g, 46%). $^1$H NMR (400 MHz, DMSO-$d_6$) δ 7.35 (s, 1H), 3.11 (td, J=5.5, 2.4 Hz, 2H), 2.80 (t, J=5.3 Hz, 2H), 2.26 (s, 1H), 1.15 (d, J=4.5 Hz, 6H).

Preparation of 3,3-Dimethyl-4-[5-(3-nitro-phenyl)-oxazol-2-yl]-piperazin-2-one (IIc)

A mixture of Intermediate IIa (500 mg, 3.90 mmol) and Intermediate IIb (900 mg, 4.01 mmol) was heated to 145° C. After 1.5 h, a further portion of IIa was added (100 mg, 0.780 mmol), then again after a further 2 h (200 mg, 1.56 mmol) with a final portion 2 h later (200 mg, 1.56 mmol). The mixture was heated for 2 h then cooled and partially dissolved in EtOH and EtOAc. The insoluble solid was recovered by filtration and the separated organic portion washed with water. The organics were dried (MgSO$_4$), filtered and evaporated to give a yellow solid which was combined with the solid recovered previously for purification by column chromatography (SiO$_2$, 5% EtOH in DCM) to afford the title compound as a yellow solid (538 mg, 65%). $^1$H NMR (400 MHz, DMSO-$d_6$) δ 8.32 (t, J=1.8 Hz, 1H), 8.19 (s, 1H), 8.06 (dd, J=8.1, 2.1 Hz, 1H), 7.99 (d, J=7.9 Hz, 1H), 7.73-7.67 (m, 2H), 3.85-3.70 (m, 2H), 3.34-3.26 (m, 2H), 1.67 (s, 6H).

Preparation of 4-[5-(3-Amino-phenyl)-oxazol-2-yl]-3,3-dimethyl-piperazin-2-one (IId)

A mixture of Intermediate IIc (900 mg, 2.84 mmol) and 10% Pd—C (100 mg) in THF (100 ml) and methanol (100 ml) was stirred under an atmosphere of H₂ at RT and ambient pressure for 4 h. The catalyst was removed by filtration and the solvent removed under vacuum to afford the title compound as an off-white solid (810 mg, 99%). ¹H NMR (400 MHz, DMSO-d₆) δ 11.35-11.32 (m, 1H), 8.17-8.01 (m, 1H), 7.16 (s, 1H), 7.03 (t, J=7.7 Hz, 1H), 6.74 (s, 1H), 6.71 (d, J=7.6 Hz, 1H), 6.45 (d, J=8.0 Hz, 1H), 5.16 (s, 2H), 3.72-3.67 (m, 2H), 3.33-3.26 (m, 2H), 1.64 (s, 6H).

Preparation of 3,3-Dimethyl-4-{5-[3-(4-methyl-pyrimidin-2-ylamino)-phenyl]-oxazol-2-yl}-piperazin-2-one (Compound 002)

A solution of Intermediate IIc (60 mg, 0.210 mmol) and 2-chloro-4-methylpyrimidine (40 mg, 0.31 mmol) in 2-propanol (3 ml) was heated to reflux for 40 h. The cooled mixture was treated with NaHCO₃ solution (sat. aqu) and extracted with EtOAc. The combined organics were dried (MgSO₄), filtered and then carefully concentrated under vacuum to provoke precipitation. The precipitate was collected by filtration, washed with ether and dried to afford the title compound as a beige solid (42 mg, 53%). ¹H NMR (400 MHz, DMSO-d₆) δ 9.63 (s, 1H), 8.34 (d, J=5.0 Hz, 1H), 8.16-8.14 (m, 1H), 8.12 (s, 11H), 7.61 (dd, J=8.1, 1.3 Hz, 1H), 7.30-7.25 (m, 2H), 7.13 (d, J=7.7 Hz, 1H), 6.75 (d, J=5.0 Hz, 1H), 3.75-3.70 (m, 2H), 3.35-3.31 (m, 2H), 2.37 (s, 3H), 1.67 (s, 6H).

Synthesis of Compound 040

Preparation of N-(2-Chloro-ethyl)-4-nitro-benzenesulfonamide (IIIa)

A stirred solution of 2-chloroethylamine hydrochloride (1.00 g, 8.62 mmol) and triethylamine (3.60 ml, 25.9 mmol) in dry DCM (25 ml) at 0° C. was treated with a solution of nosyl chloride (1.91 g, 8.62 mmol) in dry DCM (25 ml) dropwise. On complete addition, the solution was warmed to ambient temperature and stirred overnight. The solution was evaporated and the residue purified by column chromatography (SiO₂, 20% EtOAc in cyclohexane to 30% EtOAc in cyclohexane) to afford the title compound as a white solid (2.03 g, 89%). ¹H NMR (400 MHz, DMSO-d₆) δ 8.45-8.38 (m, 3H), 8.09-8.04 (m, 2H), 3.59 (t, J=6.0 Hz, 2H), 3.17 (s, 2H).

Preparation of 1-(4-Nitro-benzenesulfonyl)-aziridine (IIIb)

Intermediate IIIb was prepared according to the method of Iwaki et al, *Bioorg. Med. Chem. Lett.*, (2012), 2798. A stirred slurry of IIIa (2.00 g, 7.56 mmol) in toluene was treated with a solution of KOH (2.54 g, 45.3 mmol) in water (12 ml) in one portion then stirred at ambient temperature for 1 h. The solution was diluted with EtOAc and the organics separated, washed with brine, dried (MgSO₄), filtered and evaporated to afford the title compound as a pale yellow solid (1.41 g, 82%). ¹H NMR (400 MHz, CDCl₃) δ 8.47-8.26 (m, 1H), 8.24-8.10 (m, 1H), 2.48 (s, 2H).

Preparation of N-[2-(4-nitrophenylsulfonylamino)-ethyl] D-Valine methyl ester (IIIc)

A mixture of IIIb (2.00 g, 8.76 mmol), D-valine methyl ester hydrochloride (1.47 g, 8.76 mmol) and Na₂CO₃ (929 mg, 8.76 mmol), dry acetonitrile (50 ml) was heated to reflux

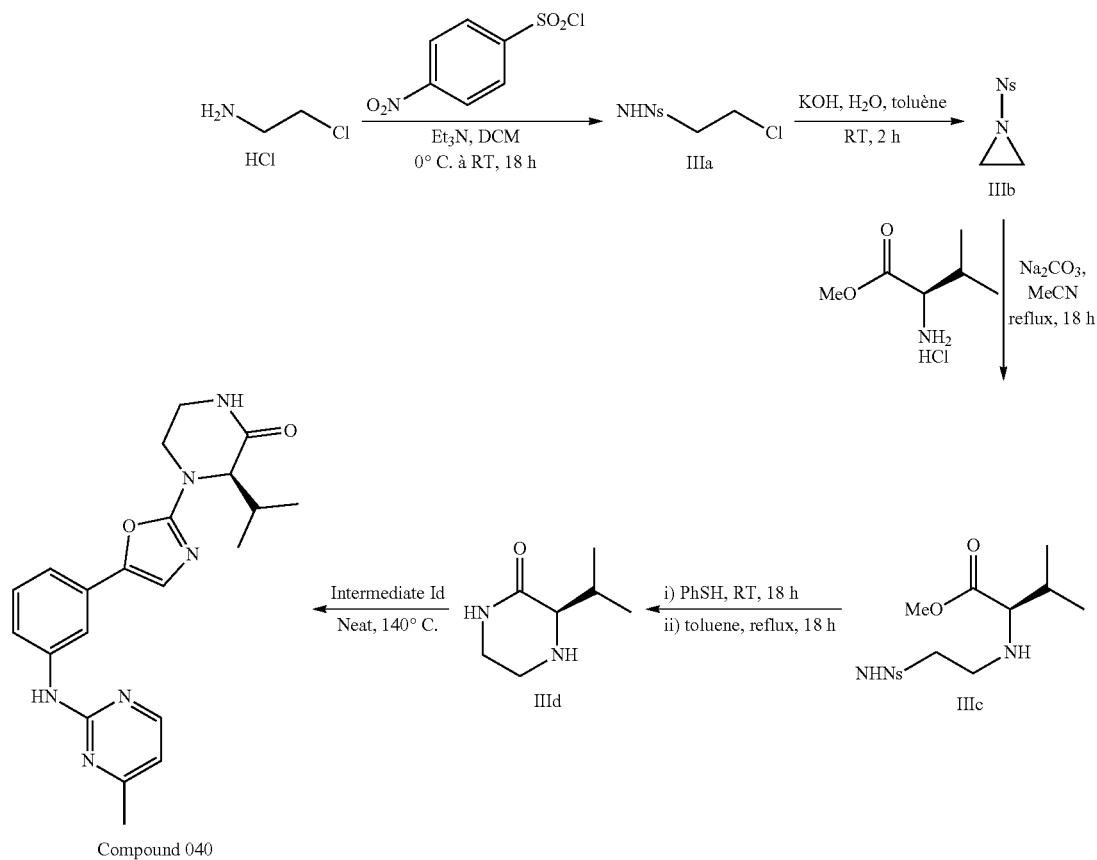

Compound 040 for 2 h. The mixture was cooled, filtered and evaporated. The residue was purified by column chromatography (SiO$_2$, 5% acetone in DCM to 10% acetone in DCM) to afford the title compound as a golden oil (2.44 g, 90%). $^1$H NMR (400 MHz, DMSO-d$_6$) δ 8.44-8.40 (m, 2H), 8.07-8.03 (m, 2H), 7.96 (s, 1H), 3.60 (s, J=3.6 Hz, 3H), 2.90-2.83 (m, 3H), 2.58-2.51 (m, 1H), 2.39-2.31 (m, 1H), 1.99 (s, 1H), 1.75 (dq, J=13.4, 6.7 Hz, 1H), 0.82 (dd, J=8.7, 6.8 Hz, 6H).

Preparation of (R)-3-Isopropyl-piperazin-2-one (IIId)

Intermediate IIId was prepared largely according to the method of Maligres et al (Tetrahedron Letters, (1997), 5253). A solution of 13 (2.44 g, 6.79 mmol) in dry acetonitrile (100 ml) was treated with K$_2$CO$_3$ (3.75 g, mmol) and thiophenol (2.08 ml, mmol) and stirred at 50° C. overnight. The mixture was evaporated under vacuum and the residue purified by column chromatography (SiO$_2$, 10:90:1 EtOH:DCM:NH$_4$OH v/v) to afford an off-white solid (909 mg). This solid was taken up in toluene and heated to reflux overnight. The cooled mixture was evaporated and the residue purified by column chromatography (SiO$_2$, 10:90:1 EtOH:DCM:NH$_4$OH (v/v) to afford IIId as a beige solid (432 mg, 45%). $^1$H NMR (400 MHz, DMSO-d$_6$) δ 7.54 (s, 1H), 3.12 (td, J=11.0, 4.3 Hz, 1H), 3.05 (d, J=3.1 Hz, 1H), 3.04-2.98 (m, 1H), 2.97-2.91 (m, 1H), 2.73-2.65 (m, 1H), 2.30-2.20 (m, 2H), 0.91 (d, J=7.1 Hz, 3H), 0.80 (d, J=6.8 Hz, 3H).

Preparation of (R)-3-isopropyl-4-{5-[3-(4-methyl-pyrimidin-2-ylamino)-phenyl]-oxazol-2-yl}-piperazin-2-one (Compound 040)

A mixture of (R)-3-isopropyl-piperazin-2-one (IIId) (200 mg, 1.41 mmol) and intermediate Id (200 mg, 0.698 mmol) was heated to 140° C. After 30 mins further IIId was added (96 mg, 0.661 mmol) and heating continued for a further 45 mins. The cooled mixture was taken up in EtOH and DCM and washed with NaHCO$_3$ sat aq soln. The organics were dried (MgSO$_4$), filtered and evaporated and the residue purified by column chromatography (SiO$_2$, 10% EtOH in DCM) to afford IIId as a beige solid (229 mg, 84%). $^1$H NMR (400 MHz, DMSO-d$_6$) δ 9.58 (s, 1H), 8.33 (d, J=5.0 Hz, 1H), 8.07 (s, 2H), 7.63 (d, J=7.6 Hz, 1H), 7.27 (t, J=8.4 Hz, 1H), 7.24 (s, 1H), 7.12 (d, J=7.7 Hz, 1H), 6.75 (d, J=5.0 Hz, 1H), 4.21 (d, J=6.0 Hz, 1H), 3.98 (dt, J=12.8, 4.2 Hz, 1H), 3.52 (ddd, J=13.1, 8.9, 4.1 Hz, 1H), 3.43-3.35 (m, 1H), 3.30-3.14 (m, 1H), 2.41-2.33 (m, 4H), 1.06 (d, J=6.8 Hz, 3H), 0.99 (d, J=6.8 Hz, 3H). Chiral UPLC: r.t.=10.1 mins, 99% e.e.

Intermediates of Synthesis

Non-commercially available 2-chloro-4-alkylpyrimidines intermediates which were used to prepare compounds listed in table 1, were prepared according to the method of Jorgensen et al (J. Am. Chem. Soc., (2011), 15686).

Preparation of 2-Chloro-4-ethylpyrimidine (IVa)

A mixture of 2,4-dichloropyrimidine (2.00 g, 13.4 mmol) and Fe(acac)$_3$ (954 mg, 2.70 mmol) in dry THF (24 ml) at −78° C. under argon was treated with a solution of ethylmagnesium bromide (1 m in THF, 16.2 ml, 16.2 mmol) dropwise. After stirring at −78° C. for 30 mins, the mixture was warmed to ambient temperature and stirred for a further hour. The mixture was again cooled to −78° C. and treated with ethylmagnesium bromide solution (10 ml, 10 mmol) and warmed to RT. The mixture was diluted with water, extracted with EtOAc and the organics dried (MgSO$_4$), filtered and evaporated. The residue was purified by column chromatography (SiO$_2$, 20% EtOAc in cyclohexane) to afford the title compound as a clear liquid (642 mg, 34%).

$^1$H NMR (400 MHz, DMSO-d$_6$) δ 8.64 (d, J=5.1 Hz, 1H), 7.47 (d, J=5.1 Hz, 1H), 2.76 (q, J=7.6 Hz, 2H), 1.21 (t, J=7.6 Hz, 3H).

The 2-chloro-4-aryl-2-ylpyrimidine and 2-chloro-4-heteroaryl-2-ylpyrimidine intermediates which were used to prepare compounds listed in table 1, were prepared by Suzuki coupling methods (See for example, N. Miyaura and A. Suzuki (Chemical Reviews, (1995), 2457)).

Preparation of 2-Chloro-4-thiophen-2-ylpyrimidine (IVb)

A mixture of 2,4-dichloropyrimidine (1.00 g, 6.71 mmol), 2-thiopheneboronic acid (430 mg, 3.36 mmol), Na$_2$CO$_3$ (0.4M solution in water, 20 ml, 8.06 mmol) and Pd(PPh$_3$)$_4$ (78 mg, 0.067 mmol) in THF (20 ml) was heated to 90° C. overnight. The cooled mixture was diluted with water, extracted with DCM and the organics dried (MgSO$_4$), filtered and evaporated. The residue was purified by column chromatography (SiO$_2$, 20% EtOAc in cyclohexane) to afford the title compound as a white solid (591 mg, 89%). $^1$H NMR (400 MHz, DMSO-d$_6$) δ 8.73 (d, J=5.3 Hz, 1H), 8.16 (dd, J=3.8, 1.1 Hz, 1H), 8.04 (d, J=5.3 Hz, 1H), 7.95 (dd, J=5.0, 1.1 Hz, 1H), 7.29 (dd, J=5.0, 3.8 Hz, 1H).

4-Amino-2-chloro-pyrimidine intermediates, which were used to prepare compounds listed in table 1, were prepared according to the method below largely based on that described in US 2006/199804.

Preparation of 4-(2-Chloro-pyrimidin-4-yl)-morpholine (IVc)

A stirred solution of 2,4-dichloropyrimidine (5.00 g, 36.5 mmol) and diisopropylethylamine (14.0 ml, 80.4 mmol) in EtOH (60 ml) at 0° C. was treated with morpholine (3.18 ml, 36.5 mmol) and allowed to warm to ambient temperature overnight. The solution was poured into brine and extracted with DCM. The organics were dried (MgSO$_4$), filtered and evaporated. The residue was purified by column chromatography (SiO$_2$, 5% EtOH in DCM) to afford the title compound IVc as a white solid (1.3 g, 36%). $^1$H NMR (300 MHz, DMSO-d$_6$) δ 8.10 (d, J=6.2 Hz, 1H), 6.83 (d, J=6.2 Hz, 1H), 3.72-3.49 (m, 8H).

Non-commercially available 2-Chloro-4-cyanopyrimidine (IVd) intermediates which was used to prepare compounds listed in table 1, were prepared according to the method described in WO2005/075468.

Preparation of 2-Chloro-4-cyanopyrimidine (IVd)

A solution of 4-methyl-1H-pyrimidin-2-one hydrochloride (14.7 g, 100 mmol) in 50% aqueous acetic acid (100 ml) at 15° C. was treated with sodium nitrite in one portion (10.4 g, 150 mmol) with vigorous stirring causing an exothermic reaction (40° C.). A yellow precipitate was filtered off, washed with cold water and dried in a vacuum dessicator to afford the 2-hydroxy-pyrimidine-4-carbaldehyde oxime intermediate as a pale yellow solid (13.1 g, 94%) $^1$H NMR (400 MHz, DMSO-d$_6$) δ 12.44 (s, 1H), 11.87 (br s, 1H), 7.92 (d, J=6.3 Hz, 1H), 7.77 (d, J=0.4 Hz, 1H), 6.66 (dd, J=6.4, 0.9 Hz, 1H). The oxime was treated with phosphorus oxychloride (20 ml) and warmed slowly to 45° C. Warming was stopped as the temperature rose suddenly to 70° C. and the mixture stirred for 3 h. Diisopropylethylamine (2 ml) was added and the mixture refluxed for 30 mins before pouring into ice and extraction with DCM. The organics were washed with water then NaHCO$_3$ (sat aqu) then again with water, dried (MgSO4), filtered and evaporated to afford Intermediate IVd as a yellow oil which crystallized on standing (1.51 g, 30%). $^1$H NMR (400 MHz, DMSO-d$_6$) δ 9.15 (d, J=4.9 Hz, 1H), 8.25 (d, J=4.9 Hz, 1H).

Compounds 001-045

By repeating the methods described above using the appropriate starting materials and conditions, the following additional analogues in table 1 were prepared and characterized.

TABLE 1

| Ex # | Chemical structure | Name | ¹H NMR/LCMS |
|---|---|---|---|
| 001 | 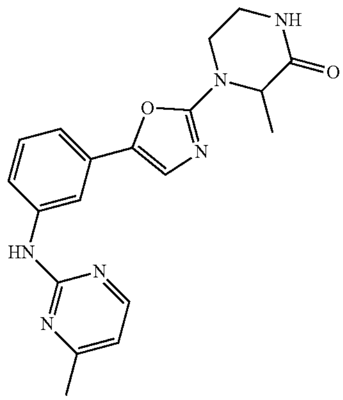 [SMILES: Cc1ccnc(Nc2cccc(-c3cnc(N4CCNC(=O)C4C)o3)c2)n1] | 3-Methyl-4-{5-[3-(4-methyl-pyrimidin-2-ylamino)-phenyl]-oxazol-2-yl}-piperazin-2-one | ¹H NMR (400 MHz, DMSO-$d_6$) δ 9.56 (s, 1H), 8.34 (d, J = 5.0 Hz, 1H), 8.10 (t, J = 1.8 Hz, 1H), 8.07 (d, J = 2.5 Hz, 1H), 7.63 (dd, J = 8.1, 1.2 Hz, 1H), 7.26 (dd, J = 13.0, 5.0 Hz, 2H), 7.13 (d, J = 7.9 Hz, 1H), 6.75 (d, J = 5.0 Hz, 1H), 4.40 (q, J = 6.9 Hz, 1H), 3.94 (dt, J = 13.0, 3.6 Hz, 1H), 3.56-3.48 (m, 1H), 3.40 (tdd, J = 9.8, 4.0, 1.0 Hz, 1H), 3.30-3.23 (m, 1H), 2.38 (s, 3H), 1.44 (d, J = 7.0 Hz, 3H) |
| 002 | 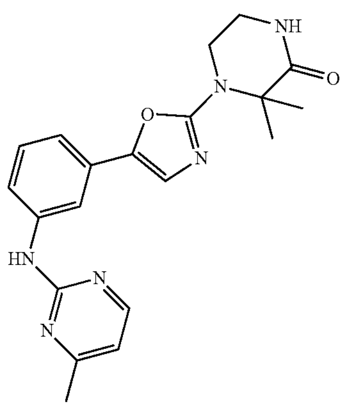 [SMILES: Cc1ccnc(Nc2cccc(-c3cnc(N4CCNC(=O)C4(C)C)o3)c2)n1] | 3,3-Dimethyl-4-{5-[3-(4-methyl-pyrimidin-2-ylamino)-phenyl]-oxazol-2-yl}-piperazin-2-one | ¹H NMR (400 MHz, DMSO-$d_6$) δ 9.63 (s, 1H), 8.34 (d, J = 5.0 Hz, 1H), 8.16-8.14 (m, 1H), 8.12 (s, 1H), 7.61 (dd, J = 8.1, 1.3 Hz, 1H), 7.30-7.25 (m, 2H), 7.13 (d, J = 7.7 Hz, 1H), 6.75 (d, J = 5.0 Hz, 1H), 3.75-3.70 (m, 2H), 3.35-3.31 (m, 2H), 2.37 (s, 3H), 1.67 (s, 6H) |
| 003 | 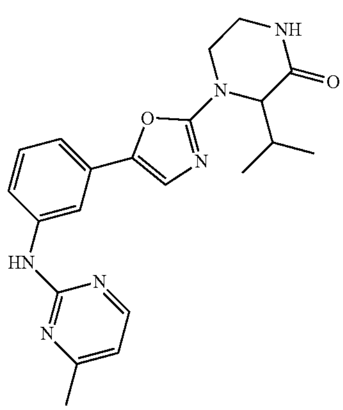 [SMILES: Cc1ccnc(Nc2cccc(-c3cnc(N4CCNC(=O)C4C(C)C)o3)c2)n1] | 3-Isopropyl-4-{5-[3-(4-methyl-pyrimidin-2-ylamino)-phenyl]-oxazol-2-yl}-piperazin-2-one | ¹H NMR (400 MHz, DMSO-$d_6$) δ 9.59 (s, 1H), 8.34 (d, J = 5.0 Hz, 1H), 8.14-8.03 (m, 2H), 7.63 (dd, J = 8.1, 1.3 Hz, 1H), 7.30-7.23 (m, 2H), 7.15-7.10 (m, 1H), 6.76 (d, J = 5.0 Hz, 1H), 4.21 (d, J = 6.0 Hz, 1H), 3.99 (dt, J = 13.1, 4.4 Hz, 1H), 3.52 (ddd, J = 12.8, 8.9, 4.1 Hz, 1H), 3.43-3.36 (m, 1H), 3.30-3.26 (m, 1H), 2.42-2.35 (m, 4H), 1.03 (dd, J = 26.2, 6.8 Hz, 6H). |

TABLE 1-continued

| Ex # | Chemical structure | Name | 1H NMR/LCMS |
|---|---|---|---|
| 004 | 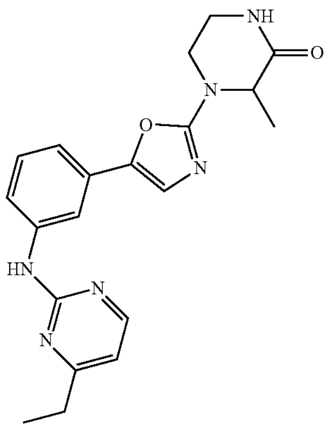 [SMILES: CCc1ccnc(Nc2cccc(-c3cnc(N4CCNC(=O)C4C)o3)c2)n1] | 4-{5-[3-(4-Ethyl-pyrimidin-2-ylamino)-phenyl]-oxazol-2-yl}-3-methyl-piperazin-2-one | 1H NMR (400 MHz, DMSO-d$_6$) δ 9.59 (s, 1H), 8.37 (d, J = 5.0 Hz, 1H), 8.16 (s, 1H), 8.11 (d, J = 3.2 Hz, 1H), 7.58 (d, J = 8.5 Hz, 1H), 7.31-7.23 (m, 2H), 7.14 (d, J = 7.8 Hz, 1H), 6.76 (d, J = 5.0 Hz, 1H), 4.40 (q, J = 7.0 Hz, 1H), 3.94 (dt, J = 12.7, 3.5 Hz, 1H), 3.57-3.47 (m, 1H), 3.44-3.38 (m, 1H), 3.26-3.20 (m, 1H), 2.66 (q, J = 7.6 Hz, 2H), 1.43 (d, J = 7.0 Hz, 3H), 1.26 (t, J = 7.6 Hz, 3H). |
| 005 | 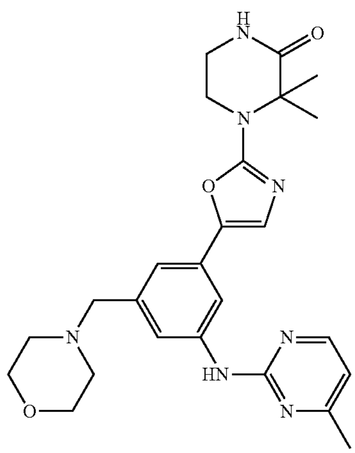 [SMILES: Cc1ccnc(Nc2cc(CN3CCOCC3)cc(-c3cnc(N4CCNC(=O)C4(C)C)o3)c2)n1] | 3,3-Dimethyl-4-{5-[3-(4-methyl-pyrimidin-2-ylamino)-5-morpholin-4-ylmethyl-phenyl]-oxazol-2-yl}-piperazin-2-one | 1H NMR (400 MHz, DMSO-d$_6$) δ 9.60 (s, 1H), 8.34 (d, J = 5.0 Hz, 1H), 8.14 (s, 1H), 8.07 (s, 1H), 7.57 (s, 1H), 7.28 (s, 1H), 7.08 (s, 1H), 6.76 (d, J = 4.9 Hz, 1H), 3.78-3.65 (m, 2H), 3.65-3.51 (m, 4H), 3.44 (s, 2H), 3.35-3.32 (m, 2H), 2.45-2.29 (m, 7H), 1.68 (s, 6H). |
| 006 | 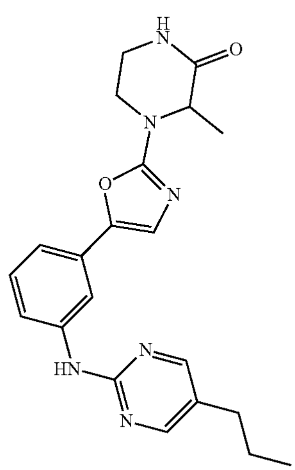 [SMILES: CCCc1cnc(Nc2cccc(-c3cnc(N4CCNC(=O)C4C)o3)c2)nc1] | 3-Methyl-4-{5-[3-(5-propyl-pyrimidin-2-ylamino)-phenyl]-oxazol-2-yl}-piperazin-2-one | 1H NMR (400 MHz, DMSO-d$_6$) δ 9.51 (s, 1H), 8.36 (s, 2H), 8.08 (d, J = 2.4 Hz, 1H), 7.93 (s, 1H), 7.68 (dd, J = 8.2, 1.5 Hz, 1H), 7.27 (t, J = 8.0 Hz, 1H), 7.24 (s, 1H), 7.12 (d, J = 7.9 Hz, 1H), 4.40 (q, J = 7.0 Hz, 1H), 3.93 (dt, J = 13.1, 3.5 Hz, 1H), 3.56-3.48 (m, 1H), 3.45-3.36 (m, 1H), 3.30-3.23 (m, 1H), 2.45 (t, J = 7.5 Hz, 2H), 1.64-1.51 (m, 2H), 1.44 (d, J = 7.0 Hz, 3H), 0.90 (t, J = 7.3 Hz, 3H). |

TABLE 1-continued

| Ex # | Chemical structure | Name | ¹H NMR/LCMS |
|---|---|---|---|
| 007 | 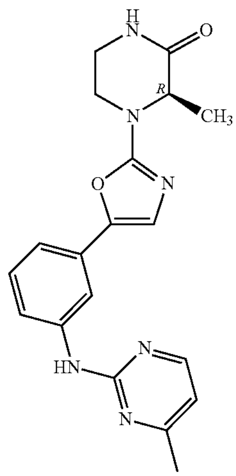 | (R)-3-Methyl-4-{5-[3-(4-methyl-pyrimidin-2-ylamino)-phenyl]-oxazol-2-yl}-piperazin-2-one | ¹H NMR (400 MHz, DMSO-$d_6$) δ 9.59 (s, 1H), 8.35 (d, J = 5.0 Hz, 1H), 8.10 (s, 2H), 7.63 (d, J = 7.4 Hz, 1H), 7.30-7.24 (m, 2H), 7.13 (d, J = 7.7 Hz, 1H), 6.76 (d, J = 5.0 Hz, 1H), 4.40 (q, J = 7.0 Hz, 1H), 3.94 (dt, J = 12.3, 3.1 Hz, 1H), 3.56-3.41 (m, 1H), 3.44-3.35 (m, 1H), 3.30-3.22 (m, 1H), 2.38 (s, 3H), 1.44 (d, J = 7.0 Hz, 3H). Chiral UPLC: r.t. = 10.2 mins, 93% e.e. |
| 008 | 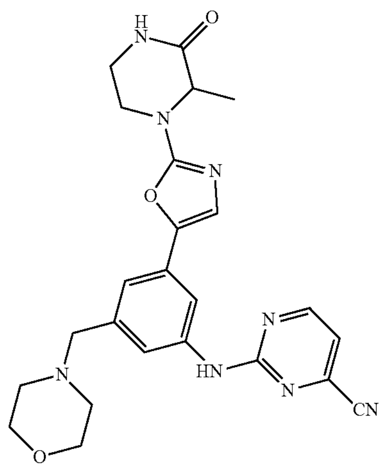 [SMILES: CC1C(=O)NCCN1c1ncc(-c2cc(CN3CCOCC3)cc(Nc3nccc(C#N)n3)c2)o1] | 2-{3-[2-(2-Methyl-3-oxo-piperazin-1-yl)-oxazol-5-yl]-5-(morpholin-4-ylmethyl)-phenylamino}-pyrimidine-4-carbonitrile | ¹H NMR (400 MHz, DMSO-$d_6$) δ 10.18 (s, 1H), 8.79 (d, J = 4.8 Hz, 1H), 8.08 (s, 1H), 7.89 (s, 1H), 7.54 (s, 1H), 7.41 (d, J = 4.7 Hz, 1H), 7.30 (s, 1H), 7.18 (s, 1H), 4.41 (q, J = 7.0 Hz, 1H), 4.00-3.92 (m, 1H), 3.63-3.60 (m, 4H), 3.59-3.50 (m, 1H), 3.47 (s, 2H), 3.46-3.36 (m, 1H), 3.30-3.23 (m, 1H), 2.44-2.37 (m, 4H), 1.45 (d, J = 7.0 Hz, 3H). |
| 009 | 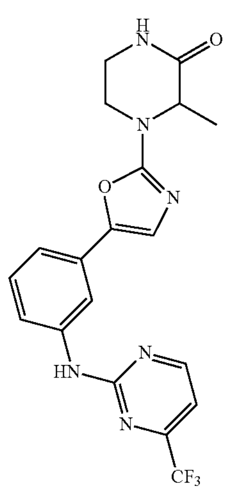 [SMILES: CC1C(=O)NCCN1c1ncc(-c2cccc(Nc3nccc(C(F)(F)F)n3)c2)o1] | 3-Methyl-4-{5-[3-((4-trifluoromethyl)-pyrimidin-2-ylamino)-phenyl]-oxazol-2-yl}-piperazin-2-one | ¹H NMR (400 MHz, DMSO-$d_6$) δ 10.27 (s, 1H), 8.84 (d, J = 4.8 Hz, 1H), 8.11 (s, 2H), 7.54 (d, J = 8.0 Hz, 1H), 7.38-7.21 (m, 4H), 4.41 (q, J = 6.9 Hz, 1H), 3.95 (dt, J = 7.0, 3.8 Hz, 1H), 3.58-3.47 (m, 1H), 3.43-3.37 (m, 1H), 3.29-3.23 (m, 1H), 1.44 (d, J = 7.0 Hz, 3H). |

TABLE 1-continued

| Ex # | Chemical structure | Name | ¹H NMR/LCMS |
|---|---|---|---|
| 010 | 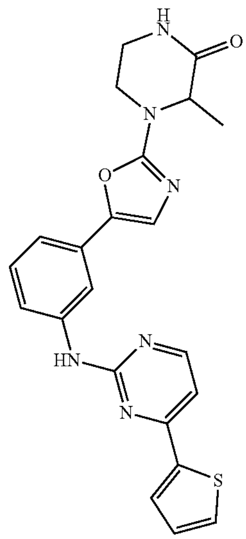 [SMILES: CC1C(=O)NCCN1c1ncc(-c2cccc(Nc3nccc(-c4cccs4)n3)c2)o1] | 3-Methyl-4-{5-[3-(4-thiophen-2-yl-pyrimidin-2-ylamino)-phenyl]-oxazol-2-yl}-piperazin-2-one | ¹H NMR (400 MHz, DMSO-d$_6$) δ 9.68 (s, 1H), 8.50 (d, J = 5.1 Hz, 1H), 8.12 (s, 1H), 8.07 (s, 1H), 8.01 (d, J = 3.7 Hz, 1H), 7.85 (d, J = 5.0 Hz, 1H), 7.64 (d, J = 8.3 Hz, 1H), 7.39-7.28 (m, 3H), 7.25 (t, J = 4.4 Hz, 1H), 7.18 (d, J = 7.7 Hz, 1H), 4.42 (d, J = 7.1 Hz, 1H), 3.95 (d, J = 13.0 Hz, 1H), 3.55-3.47 (m, 1H), 3.43-3.34 (m, 1H), 3.28-3.20 (m, 1H), 1.43 (d, J = 7.0 Hz, 3H). |
| 011 | 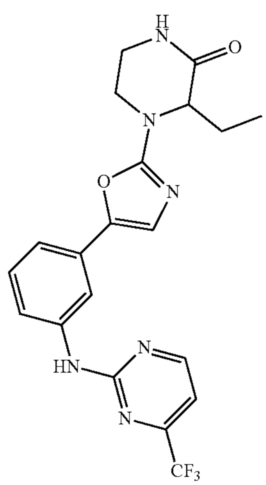 [SMILES: CCC1C(=O)NCCN1c1ncc(-c2cccc(Nc3nccc(C(F)(F)F)n3)c2)o1] | 3-Ethyl-4-{5-[3-((4-trifluoromethyl)-pyrimidin-2-ylamino)-phenyl]-oxazol-2-yl}-piperazin-2-one | ¹H NMR (400 MHz, DMSO-d$_6$) δ 10.27 (s, 1H), 8.83 (d, J = 4.9 Hz, 1H), 8.10-8.05 (m, 2H), 7.55 (dd, J = 7.7, 0.7 Hz, 1H), 7.33 (t, J = 7.9 Hz, 1H), 7.29 (d, J = 4.9 Hz, 1H), 7.27 (s, 1H), 7.23 (d, J = 7.8 Hz, 1H), 4.30 (dd, J = 8.2, 4.9 Hz, 1H), 3.96 (dt, J = 13.3, 3.5 Hz, 1H), 3.52 (ddd, J = 13.4, 9.9, 3.8 Hz, 1H), 3.44-3.36 (m, 1H), 3.28-3.21 (m, 1H), 2.03-1.94 (m, 1H), 1.92-1.83 (m, 1H), 0.95 (t, J = 7.4 Hz, 3H). |
| 012 | 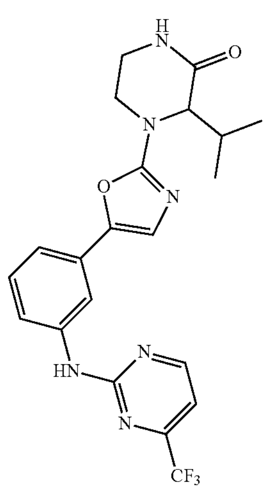 [SMILES: CC(C)C1C(=O)NCCN1c1ncc(-c2cccc(Nc3nccc(C(F)(F)F)n3)c2)o1] | 3-Isopropyl-4-{5-[3-((4-trifluoromethyl)-pyrimidin-2-ylamino)-phenyl]-oxazol-2-yl}-piperazin-2-one | ¹H NMR (400 MHz, DMSO-d$_6$) δ 10.26 (s, 1H), 8.82 (d, J = 4.9 Hz, 1H), 8.05 (d, J = 12.1 Hz, 2H), 7.56 (dd, J = 8.3, 1.5 Hz, 1H), 7.33 (t, J = 7.9 Hz, 1H), 7.28 (d, J = 5.0 Hz, 1H), 7.26 (s, 1H), 7.22 (d, J = 7.7 Hz, 1H), 4.21 (d, J = 6.3 Hz, 1H), 3.99 (dt, J = 12.9, 4.2 Hz, 1H), 3.52 (ddd, J = 13.3, 8.7, 4.2 Hz, 1H), 3.38 (s, 1H), 3.30-3.25 (m, 1H), 2.42-2.34 (m, 1H), 1.05 (d, J = 6.8 Hz, 3H), 0.99 (d, J = 6.8 Hz, 3H). |

TABLE 1-continued

| Ex # | Chemical structure | Name | ¹H NMR/LCMS |
|---|---|---|---|
| 013 | 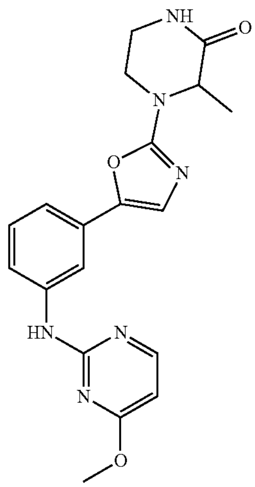 [SMILES: COc1ccnc(Nc2cccc(-c3cnc(N4CCNC(=O)C4C)o3)c2)n1] | 4-{5-[3-(4-Methoxy-pyrimidin-2-ylamino)-phenyl]-oxazol-2-yl}-3-methyl-piperazin-2-one | ¹H NMR (400 MHz, DMSO-d$_6$) δ 9.60 (s, 1H), 8.21 (d, J = 5.3 Hz, 1H), 8.10 (d, J = 2.1 Hz, 1H), 8.06 (s, 1H), 7.58 (d, J = 7.8 Hz, 1H), 7.31-7.25 (m, 2H), 7.16 (d, J = 7.7 Hz, 1H), 6.30 (d, J = 5.3 Hz, 1H), 4.38 (q, J = 6.9 Hz, 1H), 3.95 (s, 3H), 3.92-3.88 (m, 1H), 3.55-3.46 (m, 1H), 3.43-3.36 (m, 1H), 3.30-3.22 (m, 1H), 1.43 (d, J = 7.0 Hz, 3H). |
| 014 | 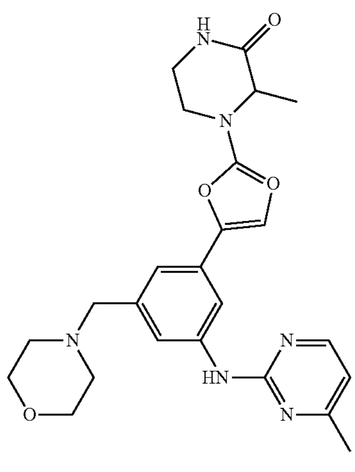 | 3-Methyl-4-{5-[3-(4-methyl-pyrimidin-2-ylamino)-5-morpholin-4-ylmethyl-phenyl]-oxazol-2-yl}-piperazin-2-one | ¹H NMR (400 MHz, DMSO-d$_6$) δ 9.52 (s, 1H), 8.35 (d, J = 5.0 Hz, 1H), 8.08 (s, 1H), 8.02 (s, 1H), 7.59 (s, 1H), 7.25 (s, 1H), 7.07 (s, 1H), 6.75 (d, J = 4.9 Hz, 1H), 4.40 (q, J = 6.9 Hz, 1H), 3.94 (dt, J = 12.7, 3.4 Hz, 1H), 3.60 (t, J = 4.4 Hz, 4H), 3.56-3.49 (m, 1H), 3.44 (s, 2H), 3.41-3.35 (m, 1H), 3.29-3.25 (m, 1H), 2.43-2.34 (m, 7H), 1.45 (d, J = 7.0 Hz, 3H). |
| 015 | 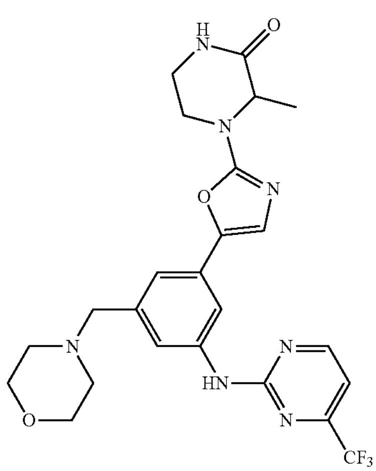 [SMILES: CC1C(=O)NCCN1c1ncc(-c2cc(CN3CCOCC3)cc(Nc3nccc(C(F)(F)F)n3)c2)o1] | 3-Methyl-4-{5-[3-morpholin-4-ylmethyl-5-((4-trifluoromethyl)-pyrimidin-2-ylamino)-phenyl]-oxazol-2-yl}-piperazin-2-one | ¹H NMR (400 MHz, DMSO-d$_6$) δ 10.21 (s, 1H), 8.83 (d, J = 4.8 Hz, 1H), 8.08 (s, 1H), 7.99 (s, 1H), 7.54 (s, 1H), 7.28 (d, J = 5.6 Hz, 2H), 7.17 (s, 1H), 4.41 (q, J = 7.1 Hz, 1H), 3.95 (d, J = 12.8 Hz, 1H), 3.64-3.56 (m, 4H), 3.56-3.49 (m, 1H), 3.46 (s, 2H), 3.43-3.36 (m, 1H), 3.29-3.23 (m, 1H), 2.39 (s, 4H), 1.44 (d, J = 7.0 Hz, 3H). |

TABLE 1-continued

| Ex # | Chemical structure | Name | ¹H NMR/LCMS |
|---|---|---|---|
| 016 | 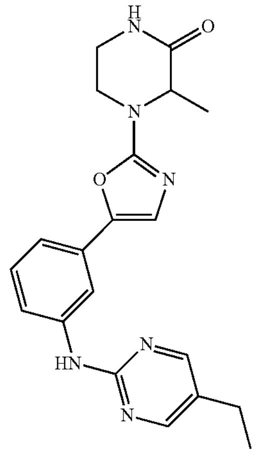 [SMILES: CCc1cnc(Nc2cccc(-c3cnc(N4CCNC(=O)C4C)o3)c2)nc1] | 4-{5-[3-(5-Ethyl-pyrimidm-2-ylamino)-phenyl]-oxazol-2-yl}-3-methyl-piperazin-2-one | ¹H NMR (400 MHz, DMSO-d₆) δ 9.51 (s, 1H), 8.38 (s, 2H), 8.08 (d, J = 1.7 Hz, 1H), 7.93 (t, J = 1.8 Hz, 1H), 7.68 (dd, J = 7.8, 1.6 Hz, 1H), 7.27 (t, J = 8.0 Hz, 1H), 7.24 (s, 1H), 7.16-7.08 (m, 1H), 4.40 (q, J = 7.0 Hz, 1H), 3.93 (dt, J = 13.5, 3.6 Hz, 1H), 3.56-3.47 (m, 1H), 3.44-3.35 (m, 1H), 3.30-3.23 (m, 1H), 2.54-2.51 (m, 2H), 1.44 (d, J = 7.0 Hz, 3H), 1.18 (t, J = 7.6 Hz, 3H). |
| 017 | 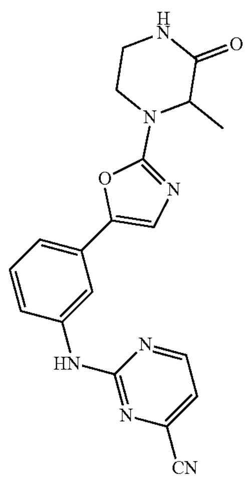 [SMILES: CC1C(=O)NCCN1c1ncc(-c2cccc(Nc3nccc(C#N)n3)c2)o1] | 2-{3-[2-(2-Methyl-3-oxo-piperazin-1-yl)-oxazol-5-yl]-phenylamino}-pyrimidine-4-carbonitrile | ¹H NMR (400 MHz, DMSO-d₆) δ 10.22 (s, 1H), 8.79 (d, J = 4.7 Hz, 1H), 8.07 (s, 1H), 7.98 (s, 1H), 7.55 (d, J = 8.0 Hz, 1H), 7.41 (d, J = 4.6 Hz, 1H), 7.35 (t, J = 7.8 Hz, 1H), 7.30 (s, 1H), 7.25 (d, J = 7.6 Hz, 1H), 4.40 (q, J = 7.1 Hz, 1H), 3.96 (dt, J = 7.0, 4.1 Hz, 1H), 3.57-3.50 (m, 1H), 3.40 (td, J = 11.1, 4.2 Hz, 1H), 3.29-3.23 (m, 1H), 1.45 (d, J = 7.1 Hz, 3H). |
| 018 | 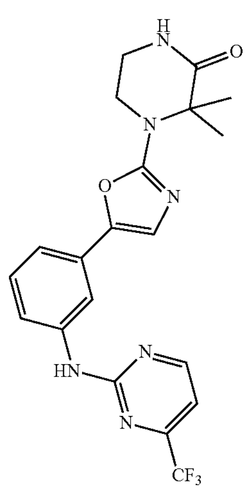 [SMILES: CC1(C)C(=O)NCCN1c1ncc(-c2cccc(Nc3nccc(C(F)(F)F)n3)c2)o1] | 3,3-Dimethyl-4-{5-[3-((4-trifluoromethyl)-pyrimidin-2-ylamino)-phenyl]-oxazol-2-yl}-piperazin-2-one | ¹H NMR (400 MHz, DMSO-d₆) δ 10.30 (s, 1H), 8.83 (d, J = 4.8 Hz, 1H), 8.22-8.02 (m, 2H), 7.59 (d, J = 8.1 Hz, 1H), 7.43-7.17 (m, 4H), 3.83-3.65 (m, 2H), 3.38-3.32 (m, 2H), 1.68 (s, 6H). |

TABLE 1-continued

| Ex # | Chemical structure | Name | ¹H NMR/LCMS |
|---|---|---|---|
| 019 | 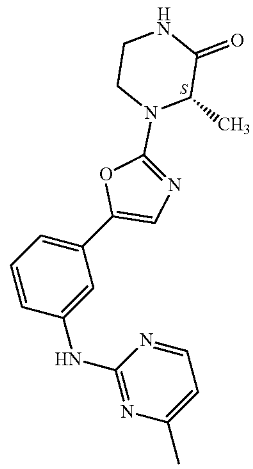 | (S)-3-Methyl-4-{5-[3-(4-methyl-pyrimidin-2-ylamino)-phenyl]-oxazol-2-yl}-piperazin-2-one | ¹H NMR (400 MHz, DMSO-d$_6$) δ 9.59 (s, 1H), 8.35 (s, 1H), 8.10 (s, 2H), 7.63 (d, J = 8.1 Hz, 1H), 7.34-7.20 (m, 2H), 7.13 (d, J = 7.6 Hz, 1H), 6.76 (s, 1H), 4.40 (dd, J = 14.1, 7.0 Hz, 1H), 3.93 (d, J = 11.1 Hz, 1H), 3.58-3.45 (m, 1H), 3.45-3.37 (m, 1H), 3.29-3.20 (m, 1H), 2.37 (s, 3H), 1.44 (d, J = 6.6 Hz, 3H). Chiral UPLC : r.t. = 11.8 mins, 87% e.e. |
| 020 | 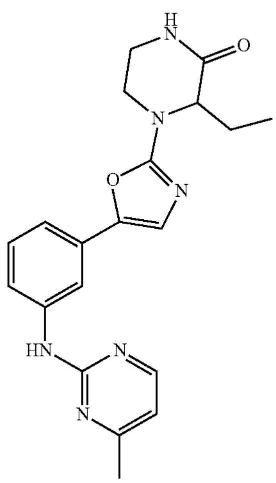 [SMILES: CCC1C(=O)NCCN1c1ncc(-c2cccc(Nc3nccc(C)n3)c2)o1] | 3-Ethyl-4-{5-[3-(4-methyl-pyrimidin-2-ylamino)-phenyl]-oxazol-2-yl}-piperazin-2-one | ¹H NMR (400 MHz, DMSO-d$_6$) δ 9.56 (s, 1H), 8.34 (d, J = 5.0 Hz, 1H), 8.08 (s, 1H), 8.05 (s, 1H), 7.63 (dd, J = 8.1, 1.3 Hz, 1H), 7.27 (t, J = 7.9 Hz, 1H), 7.24 (s, 1H), 7.13 (d, J = 7.8 Hz, 1H), 6.75 (d, J = 5.0 Hz, 1H), 4.30 (dd, J = 8.1, 5.0 Hz, 1H), 3.96 (dt, J = 13.2, 3.7 Hz, 1H), 3.52 (ddd, J = 13.4, 9.8, 3.8 Hz, 1H), 3.45-3.33 (m, 1H), 3.29-3.21 (m, 1H), 2.37 (s, 3H), 2.07-1.94 (m, 1H), 1.89 (d, J = 7.6 Hz, 1H), 0.96 (t, J = 7.4 Hz, 3H). |
| 021 | 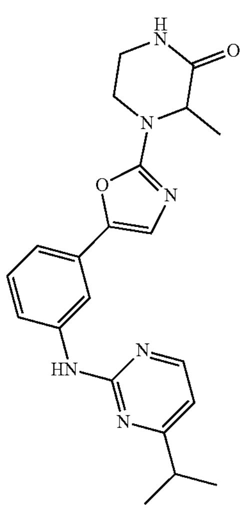 [SMILES: CC(C)c1ccnc(Nc2cccc(-c3cnc(N4CCNC(=O)C4C)o3)c2)n1] | 4-{5-[3-(4-Isopropyl-pyrimidin-2-ylamino)-phenyl]-oxazol-2-yl}-3-methyl-piperazin-2-one | ¹H NMR (400 MHz, DMSO-d$_6$) δ 9.54 (s, 1H), 8.38 (d, J = 5.0 Hz, 1H), 8.20 (s, 1H), 8.06 (s, 1H), 7.55 (d, J = 8.2 Hz, 1H), 7.27 (t, J = 8.0 Hz, 1H), 7.24 (s, 1H), 7.14 (d, J = 7.1 Hz, 1H), 6.77 (d, J = 5.0 Hz, 1H), 4.41 (q, J = 7.0 Hz, 1H), 3.94 (dt, J = 12.8, 2.8 Hz, 1H), 3.55-3.47 (m, 1H), 3.45-3.38 (m, 1H), 3.28-3.20 (m, 1H), 2.98-2.82 (m, 1H), 1.43 (d, J = 7.1 Hz, 3H), 1.27 (d, J = 6.9 Hz, 6H). |

TABLE 1-continued

| Ex # | Chemical structure | Name | ¹H NMR/LCMS |
|---|---|---|---|
| 022 | 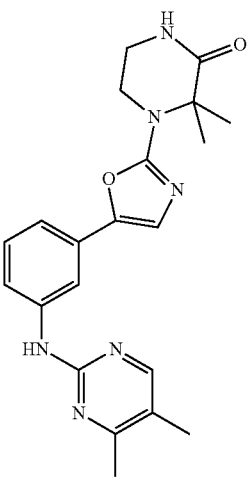 [SMILES: Cc1cnc(Nc2cccc(-c3cnc(N4CCNC(=O)C4(C)C)o3)c2)nc1C] | 4-{5-[3-(4,5-Dimethyl-pyrimidin-2-ylamino)-phenyl]-oxazol-2-yl}-3,3-dimethyl-piperazin-2-one | ¹H NMR (400 MHz, DMSO-d₆) δ 9.50 (s, 1H), 8.18-8.13 (m, 3H), 7.59 (dd, J = 8.1, 1.2 Hz, 1H), 7.29-7.23 (m, 2H), 7.10 (d, J = 7.7 Hz, 1H), 3.74-3.69 (m, 2H), 3.33-3.26 (m, 2H), 2.35 (s, 3H), 2.12 (s, 3H), 1.67 (s, 6H). |
| 023 | 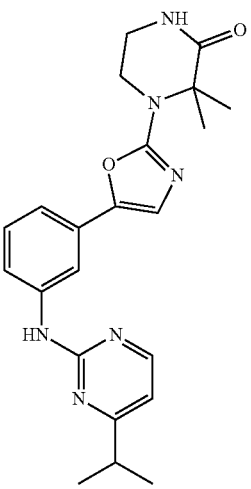 [SMILES: CC(C)c1ccnc(Nc2cccc(-c3cnc(N4CCNC(=O)C4(C)C)o3)c2)n1] | 4-{5-[3-(4-Isopropyl-pyrimidin-2-ylamino)-phenyl]-oxazol-2-yl}-3,3-dimethyl-piperazin-2-one | ¹H NMR (400 MHz, DMSO-d₆) δ 9.64 (s, 1H), 8.38 (d, J = 5.1 Hz, 1H), 8.15 (s, 2H), 7.62 (d, J = 8.3 Hz, 1H), 7.32-7.25 (m, 2H), 7.13 (d, J = 7.8 Hz, 1H), 6.78 (d, J = 5.1 Hz, 1H), 3.74-3.70 (m, 2H), 3.33-3.27 (m, 2H), 2.89 (dt, J = 13.8, 6.8 Hz, 1H), 1.67 (s, 6H), 1.25 (d, J = 6.9 Hz, 6H). |
| 024 | 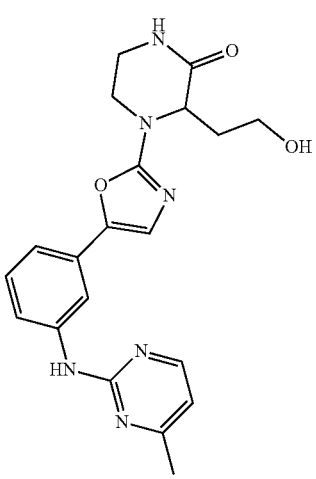 [SMILES: Cc1ccnc(Nc2cccc(-c3cnc(N4CCNC(=O)C4CCO)o3)c2)n1] | 3-(2-Hydroxy-ethyl)-4-{5-[3-(4-methyl-pyrimidin-2-ylamino)-phenyl]-oxazol-2-yl}-piperazin-2-one | ¹H NMR (400 MHz, DMSO-d₆) δ 9.55 (s, 1H), 8.34 (d, J = 5.0 Hz, 1H), 8.08 (t, J = 1.8 Hz, 1H), 8.04 (d, J = 3.1 Hz, 1H), 7.62 (ddd, J = 8.1, 2.0, 0.9 Hz, 1H), 7.27 (t, J = 7.9 Hz, 1H), 7.24 (s, 1H), 7.15-7.12 (m, 1H), 6.75 (d, J = 5.0 Hz, 1H), 4.59 (t, J = 5.3 Hz, 1H), 4.47 (dd, J = 8.2, 4.9 Hz, 1H), 3.97 (dt, J = 13.3, 3.8 Hz, 1H), 3.57-3.48 (m, 3H), 3.43-3.36 (m, 1H), 3.27-3.22 (m, 1H), 2.38 (s, 3H), 2.12-1.93 (m, 2H). |

TABLE 1-continued

| Ex # | Chemical structure | Name | $^1$H NMR/LCMS |
|---|---|---|---|
| 025 | 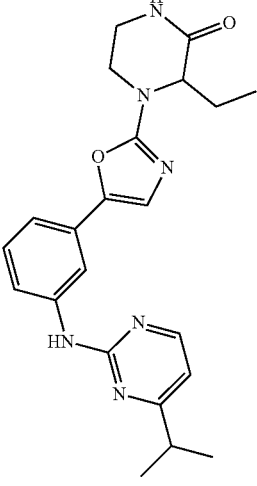 | 3-Ethyl-4-{5-[3-(4-isopropyl-pyrimidin-2-ylamino)-phenyl]-oxazol-2-yl}-piperazin-2-one | $^1$H NMR (400 MHz, DMSO-d$_6$) δ 9.56 (s, 1H), 8.38 (d, J = 5.0 Hz, 1H), 8.18 (s, 1H), 8.05 (s, 1H), 7.58 (dd, J = 8.2, 1.2 Hz, 1H), 7.28 (t, J = 7.9 Hz, 1H), 7.24 (s, 1H), 7.14 (d, J = 1.9 Hz, 1H), 6.78 (d, J = 5.1 Hz, 1H), 4.32 (dd, J = 8.1, 5.0 Hz, 1H), 3.97 (dt, J = 13.4, 3.8 Hz, 1H), 3.53 (ddd, J = 13.4, 9.9, 3.8 Hz, 1H), 3.44-3.35 (m, 1H), 3.29-3.23 (m, 1H), 2.90 (dt, J = 13.8, 6.9 Hz, 1H), 2.05-1.94 (m, 1H), 1.94-1.84 (m, 1H), 1.27 (dd, J = 6.9, 1.2 Hz, 6H), 0.96 (t, J = 7.4 Hz, 3H). |
| 026 | 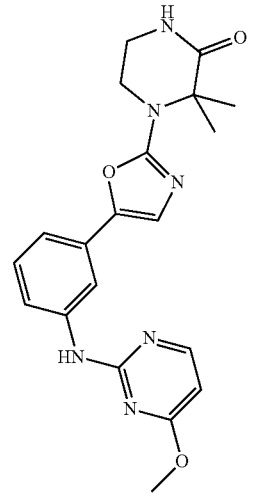 [SMILES: COc1ccnc(Nc2cccc(-c3cnc(N4CCNC(=O)C4(C)C)o3)c2)n1] | 4-{5-[3-(4-Methoxy-pyrimidin-2-ylamino)-phenyl]-oxazol-2-yl}-3,3-dimethyl-piperazin-2-one | $^1$H NMR (400 MHz, DMSO-d$_6$) δ 9.61 (s, 1H), 8.21 (d, J = 5.6 Hz, 1H), 8.12 (s, 1H), 8.05 (t, J = 1.6 Hz, 1H), 7.63 (dd, J = 8.2, 1.3 Hz, 1H), 7.30 (t, J = 8.0 Hz, 1H), 7.27 (s, 1H), 7.15 (d, J = 7.8 Hz, 1H), 6.30 (d, J = 5.7 Hz, 1H), 3.94 (s, 3H), 3.73-3.69 (m, 2H), 3.36-3.32 (m, 2H), 1.66 (s, 6H). |
| 027 | 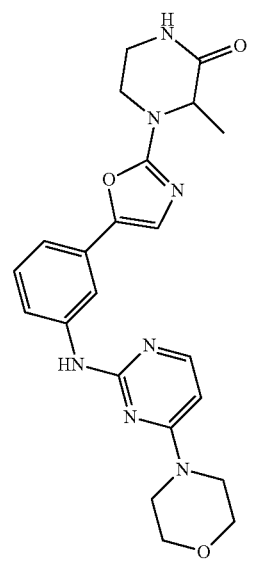 [SMILES: CC1C(=O)NCCN1c1ncc(-c2cccc(Nc3nccc(N4CCOCC4)n3)c2)o1] | 3-Methyl-4-{5-[3-(4-morpholin-4-yl-pyrimidin-2-ylamino)-phenyl]-oxazol-2-yl}-piperazin-2-one | $^1$H NMR (400 MHz, DMSO-d$_6$) δ 9.10 (s, 1H), 8.07 (d, J = 2.4 Hz, 1H), 8.01 (d, J = 6.0 Hz, 1H), 7.91 (d, J = 1.6 Hz, 1H), 7.59 (dd, J = 8.1, 1.0 Hz, 1H), 7.25 (t, J = 7.9 Hz, 1H), 7.20 (s, 1H), 7.09 (d, J = 7.7 Hz, 1H), 6.28 (d, J = 6.1 Hz, 1H), 4.39 (q, J = 7.1 Hz, 1H), 3.93 (dt, J = 13.7, 3.6 Hz, 1H), 3.70-3.65 (m, 4H), 3.59 (d, J = 4.8 Hz, 4H), 3.55-3.47 (m, 1H), 3.44-3.35 (m, 1H), 3.29-3.21 (m, 1H), 1.43 (d, J = 7.0 Hz, 3H). |

TABLE 1-continued

| Ex # | Chemical structure | Name | ¹H NMR/LCMS |
|---|---|---|---|
| 028 | 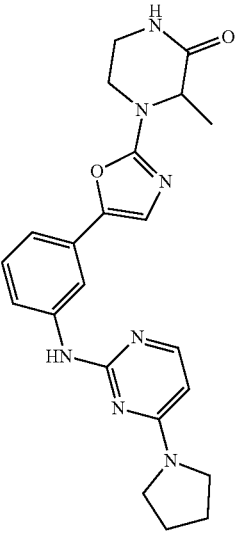 [SMILES: CC1C(=O)NCCN1c1ncc(-c2cccc(Nc3nccc(N4CCCC4)n3)c2)o1] | 3-Methyl-4-{5-[3-(4-pyrrolidin-1-yl-pyrimidin-2-ylamino)-phenyl]-oxazol-2-yl}-piperazin-2-one | ¹H NMR (400 MHz, DMSO-$d_6$) δ 9.03 (s, 1H), 8.13-8.11 (m, 1H), 8.07 (d, J = 2.6 Hz, 1H), 7.92 (d, J = 5.9 Hz, 1H), 7.59 (dd, J = 8.1, 1.1 Hz, 1H), 7.23 (t, J = 7.9 Hz, 1H), 7.19 (s, 1H), 7.07 (d, J = 7.9 Hz, 1H), 5.95 (d, J = 5.9 Hz, 1H), 4.39 (q, J = 7.0 Hz, 1H), 3.92 (dt, J = 6.8, 3.7 Hz, 1H), 3.57-3.35 (m, 6H), 3.29-3.19 (m, 1H), 1.95 (s, 4H), 1.43 (d, J = 7.0 Hz, 3H). |
| 029 | 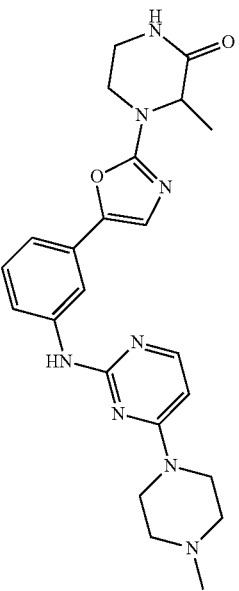 [SMILES: CC1C(=O)NCCN1c1ncc(-c2cccc(Nc3nccc(N4CCN(C)CC4)n3)c2)o1] | 3-Methyl-4-(5-{3-[4-(4-methyl-piperazin-1-yl)-pyrimidin-2-ylamino]-phenyl}-oxazol-2-yl)-piperazin-2-one | ¹H NMR (400 MHz, DMSO-$d_6$) δ 9.07 (s, 1H), 8.07 (d, J = 2.4 Hz, 1H), 7.97 (d, J = 6.1 Hz, 1H), 7.95 (t, J = 1.7 Hz, 1H), 7.55 (dd, J = 8.2, 1.1 Hz, 1H), 7.24 (t, J = 7.9 Hz, 1H), 7.19 (s, 1H), 7.09 (d, J = 7.8 Hz, 1H), 6.28 (d, J = 6.1 Hz, 1H), 4.39 (q, J = 6.9 Hz, 1H), 3.93 (dt, J = 12.6, 3.5 Hz, 1H), 3.63-3.57 (m, 4H), 3.55-3.47 (m, 1H), 3.43-3.34 (m, 1H), 3.28-3.22 (m, 1H), 2.37 (t, J = 4.9 Hz, 4H), 2.21 (s, 3H), 1.43 (d, J = 7.0 Hz, 3H). |

TABLE 1-continued

| Ex # | Chemical structure | Name | $^1$H NMR/LCMS |
|---|---|---|---|
| 030 | 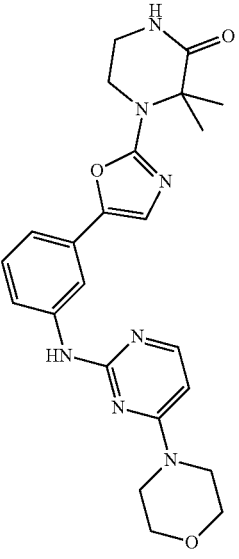 [SMILES: CC1(C)C(=O)NCCN1c1ncc(-c2cccc(Nc3nccc(N4CCOCC4)n3)c2)o1] | 3,3-Dimethyl-4-{5-[3-(4-morpholin-4-yl-pyrimidin-2-ylamino)-phenyl]-oxazol-2-yl}-piperazin-2-one | $^1$H NMR (400 MHz, DMSO-d$_6$) δ 9.17 (s, 1H), 8.14 (t, J = 2.5 Hz, 1H), 8.01 (d, J = 6.0 Hz, 1H), 7.95 (t, J = 1.7 Hz, 1H), 7.62 (dd, J = 8.2, 1.3 Hz, 1H), 7.27 (t, J = 7.9 Hz, 1H), 7.23 (s, 1H), 7.09 (d, J = 8.1 Hz, 1H), 6.29 (d, J = 6.1 Hz, 1H), 3.74-3.66 (m, 6H), 3.61-3.57 (m, 4H), 3.32-3.28 (m, 2H), 1.67 (s, 6H). |
| 031 | 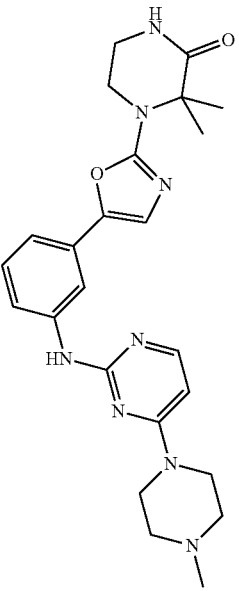 [SMILES: CN1CCN(c2ccnc(Nc3cccc(-c4cnc(N5CCNC(=O)C5(C)C)o4)c3)n2)CC1] | 3,3-Dimethyl-4-(5-{3-[4-(4-methyl-piperazin-1-yl)-pyrimidin-2-ylamino]-phenyl}-oxazol-2-yl)-piperazin-2-one | $^1$H NMR (400 MHz, DMSO-d$_6$) δ 9.12 (s, 1H), 8.12 (s, 1H), 8.01-7.95 (m, 2H), 7.60 (d, J = 7.8 Hz, 1H), 7.26 (t, J = 7.9 Hz, 1H), 7.21 (s, 1H), 7.09 (d, J = 7.4 Hz, 1H), 6.29 (d, J = 6.0 Hz, 1H), 3.74-3.69 (m, 2H), 3.65-3.58 (m, 4H), 2.50-2.42 (m, 2H), 2.39-2.35 (m, 4H), 2.22 (s, 3H), 1.67 (s, 6H). |

| Ex # | Chemical structure | Name | 1H NMR/LCMS |
|---|---|---|---|
| 032 | 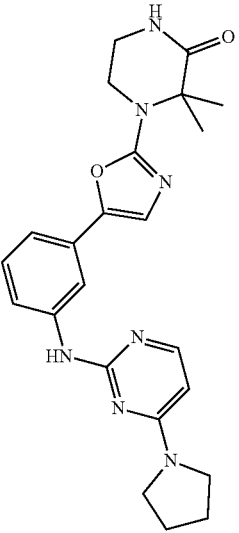 [SMILES: CC1(C)C(=O)NCCN1c1ncc(-c2cccc(Nc3nccc(N4CCCC4)n3)c2)o1] | 3,3-Dimethyl-4-{5-[3-(4-pyrrolidin-1-yl-pyrimidin-2-ylamino)-phenyl]-oxazol-2-yl}-piperazin-2-one | 1H NMR (400 MHz, DMSO-$d_6$) δ 9.09 (s, 1H), 8.13 (s, 1H), 8.08 (s, 1H), 7.92 (dd, J = 5.9, 0.6 Hz, 1H), 7.67 (d, J = 8.1 Hz, 1H), 7.25 (t, J = 7.9 Hz, 1H), 7.21 (s, 1H), 7.07 (d, J = 7.6 Hz, 1H), 5.96 (d, J = 5.8 Hz, 1H), 3.74-3.69 (m, 2H), 3.60-3.38 (m, 4H), 3.28-3.17 (m, 2H), 1.95 (s, 4H), 1.66 (s, 6H). |
| 033 | 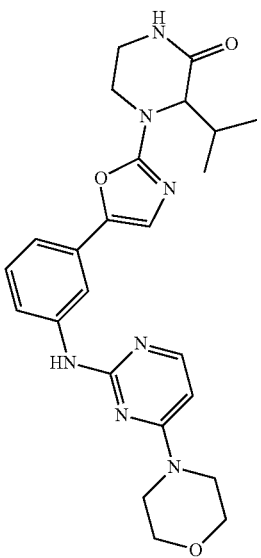 [SMILES: CC(C)C1C(=O)NCCN1c1ncc(-c2cccc(Nc3nccc(N4CCOCC4)n3)c2)o1] | 3-Isopropyl-4-{5-[3-(4-morpholin-4-yl-pyrimidin-2-ylamino)-phenyl]-oxazol-2-yl}-piperazin-2-one | 1H NMR (400 MHz, DMSO-$d_6$) δ 9.12 (s, 1H), 8.08 (s, 1H), 8.01 (d, J = 6.0 Hz, 1H), 7.93-7.91 (m, 1H), 7.59 (dd, J = 8.2, 1.2 Hz, 1H), 7.25 (t, J = 7.9 Hz, 1H), 7.20 (s, 1H), 7.09 (d, J = 7.8 Hz, 1H), 6.29 (d, J = 6.1 Hz, 1H), 4.21 (d, J = 6.0 Hz, 1H), 3.98 (dt, J = 13.4, 4.3 Hz, 1H), 3.70-3.67 (m, 4H), 3.61-3.57 (m, 4H), 3.52 (ddd, J = 13.1, 8.8, 4.1 Hz, 1H), 3.42-3.38 (m, 1H), 3.30-3.26 (m, 1H), 2.37 (dt, J = 13.1, 6.5 Hz, 1H), 1.06 (d, J = 6.8 Hz, 3H), 1.00 (d, J = 6.9 Hz, 3H). |

| Ex # | Chemical structure | Name | ¹H NMR/LCMS |
|---|---|---|---|
| 034 | 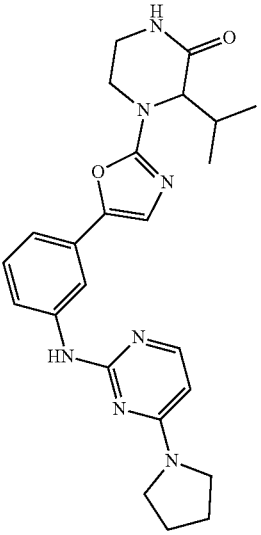 [SMILES: CC(C)C1C(=O)NCCN1c1ncc(-c2cccc(Nc3nccc(N4CCCC4)n3)c2)o1] | 3-Isopropyl-4-{5-[3-(4-pyrrolidin-1-yl-pyrimidin-2-ylamino)-phenyl]-oxazol-2-yl}-piperazin-2-one | ¹H NMR (400 MHz, DMSO-$d_6$) δ 9.04 (s, 1H), 8.11-8.06 (m, 2H), 7.92 (d, J = 5.9 Hz, 1H), 7.62 (dd, J = 7.9, 1.3 Hz, 1H), 7.24 (t, J = 7.9 Hz, 1H), 7.19 (s, 1H), 7.07 (d, J = 7.8 Hz, 1H), 5.96 (d, J = 5.9 Hz, 1H), 4.21 (d, J = 6.0 Hz, 1H), 3.97 (dt, J = 12.9, 4.2 Hz, 1H), 3.56-3.49 (m, 1H), 3.42-3.34 (m, 3H), 3.30-3.24 (m, 3H), 2.42-2.33 (m, 1H), 1.96 (s, 4H), 1.05 (d, J = 6.8 Hz, 3H), 0.99 (d, J = 6.9 Hz, 3H). |
| 035 | 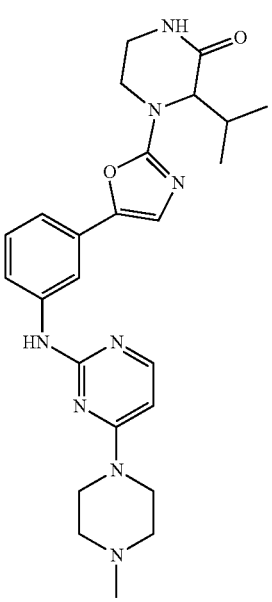 [SMILES: CC(C)C1C(=O)NCCN1c1ncc(-c2cccc(Nc3nccc(N4CCN(C)CC4)n3)c2)o1] | 3-Isopropyl-4-(5-{3-[4-(4-methyl-piperazin-1-yl)-pyrimidin-2-ylamino]-phenyl}-oxazol-2-yl)-piperazin-2-one | ¹H NMR (400 MHz, DMSO-$d_6$) δ 9.08 (s, 1H), 8.07 (s, 1H), 7.98 (d, J = 6.1 Hz, 1H), 7.96 (t, J = 1.7 Hz, 1H), 7.56 (dd, J = 8.2, 1.3 Hz, 1H), 7.25 (t, J = 7.9 Hz, 1H), 7.18 (s, 1H), 7.08 (d, J = 7.9 Hz, 1H), 6.29 (d, J = 6.1 Hz, 1H), 4.21 (d, J = 6.0 Hz, 1H), 3.98 (dt, J = 13.3, 4.4 Hz, 1H), 3.63-3.58 (m, 4H), 3.52 (ddd, J = 13.2, 8.9, 4.2 Hz, 1H), 3.42-3.33 (m, 1H), 3.30-3.25 (m, 1H), 2.39-2.36 (m, 1H), 2.22 (s, 3H), 1.05 (d, J = 6.8 Hz, 3H), 1.00 (d, J = 6.8 Hz, 3H). |

TABLE 1-continued

| Ex # | Chemical structure | Name | ¹H NMR/LCMS |
|---|---|---|---|
| 036 | 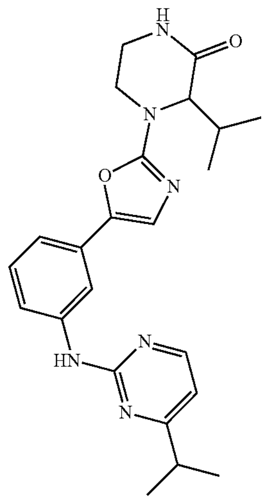 [SMILES: CC(C)c1ccnc(Nc2cccc(-c3cnc(N4CCNC(=O)C4C(C)C)o3)c2)n1] | 3-Isopropyl-4-{5-[3-(4-isopropyl-pyrimidin-2-ylamino)-phenyl]-oxazol-2-yl}-piperazin-2-one | ¹H NMR (400 MHz, DMSO-d₆) δ 9.57 (s, 1H), 8.37 (d, J = 5.0 Hz, 1H), 8.14 (s, 1H), 8.07 (s, 1H), 7.59 (d, J = 7.5 Hz, 1H), 7.27 (t, J = 8.0 Hz, 1H), 7.23 (s, 1H), 7.13 (d, J = 8.0 Hz, 1H), 6.77 (d, J = 5.1 Hz, 1H), 4.22 (d, J = 6.0 Hz, 1H), 3.99 (dt, J = 13.0, 4.3 Hz, 1H), 3.52 (ddd, J = 13.1, 8.8, 4.2 Hz, 1H), 3.42-3.33 (m, 1H), 3.29-3.25 (m, 1H), 2.89 (dt, J = 13.9, 7.0 Hz, 1H), 2.38 (td, J = 13.3, 6.6 Hz, 1H), 1.26 (d, J = 6.8 Hz, 6H), 1.05 (d, J = 6.8 Hz, 3H), 0.99 (d, J = 6.9 Hz, 3H). |
| 037 | 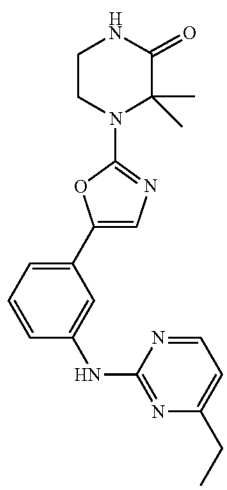 [SMILES: CCc1ccnc(Nc2cccc(-c3cnc(N4CCNC(=O)C4(C)C)o3)c2)n1] | 4-{5-[3-(4-Ethyl-pyrimidin-2-ylamino)-phenyl]-oxazol-2-yl}-3,3-dimethyl-piperazin-2-one | ¹H NMR (400 MHz, DMSO-d₆) δ 9.63 (s, 1H), 8.37 (d, J = 5.0 Hz, 1H), 8.16-8.15 (m, 1H), 8.14 (s, 1H), 7.62 (dd, J = 7.9, 1.6 Hz, 1H), 7.31-7.27 (m, 2H), 7.14 (d, J = 7.8 Hz, 1H), 6.77 (d, J = 5.0 Hz, 1H), 3.75-3.71 (m, 2H), 3.17 (d, J = 5.2 Hz, 2H), 2.66 (q, J = 7.6 Hz, 2H), 1.68 (s, 6H), 1.25 (t, J = 7.6 Hz, 3H). |
| 038 | 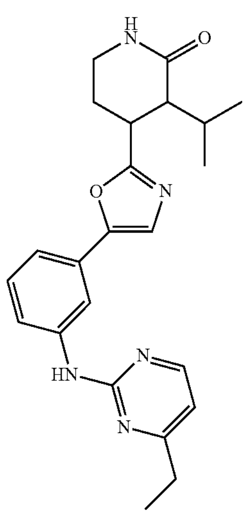 [SMILES: CCc1ccnc(Nc2cccc(-c3cnc(C4CCNC(=O)C4C(C)C)o3)c2)n1] | 4-{5-[3-(4-Ethyl-pyrimidin-2-ylamino)-phenyl]-oxazol-2-yl}-3-isopropyl-piperazin-2-one | ¹H NMR (400 MHz, DMSO-d₆) δ 9.58 (s, 1H), 8.36 (d, J = 5.0 Hz, 1H), 8.11 (s, 1H), 8.07 (s, 1H), 7.61 (dd, J = 7.8, 1.5 Hz, 1H), 7.27 (t, J = 1.9 Hz, 1H), 7.23 (s, 1H), 7.12 (d, J = 1.1 Hz, 1H), 6.76 (d, J = 5.0 Hz, 1H), 4.21 (d, J = 6.0 Hz, 1H), 3.98 (dt, J = 8.8, 4.1 Hz, 1H), 3.52 (ddd, J = 13.2, 9.1, 4.4 Hz, 1H), 3.42-3.34 (m, 1H), 3.30-3.24 (m, 1H), 2.66 (q, J = 7.6 Hz, 2H), 2.37 (dt, J = 14.5, 7.4 Hz, 1H), 1.26 (t, J = 7.6 Hz, 3H), 1.05 (d, J = 6.8 Hz, 3H), 0.99 (d, J = 6.8 Hz, 3H). |

TABLE 1-continued

| Ex # | Chemical structure | Name | ¹H NMR/LCMS |
|---|---|---|---|
| 039 | 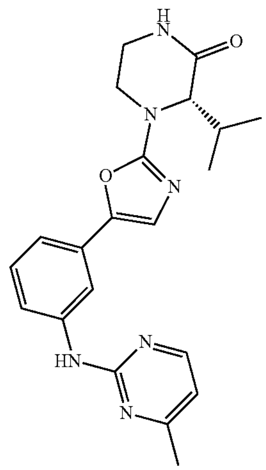 [SMILES: Cc1ccnc(Nc2cccc(-c3cnc(N4CCNC(=O)[C@@H]4C(C)C)o3)c2)n1] | (S)-3-Isopropyl-4-{5-[3-(4-methyl-pyrimidin-2-ylamino)-phenyl]-oxazol-2-yl}-piperazin-2-one | ¹H NMR (400 MHz, DMSO-$d_6$) δ 9.58 (s, 1H), 8.34 (d, J = 5.0 Hz, 1H), 8.07 (s, 2H), 7.63 (d, J = 8.0 Hz, 1H), 7.27 (t, J = 7.9 Hz, 1H), 7.24 (s, 1H), 7.12 (d, J = 7.5 Hz, 1H), 6.75 (d, J = 5.0 Hz, 1H), 4.20 (d, J = 5.9 Hz, 1H), 3.98 (dt, J = 13.1, 4.2 Hz, 1H), 3.57-3.47 (m, 1H), 3.42-3.33 (m, 1H), 3.28-3.24 (m, 1H), 2.44-2.29 (m, 4H), 1.03 (dd, J = 26.0, 6.8 Hz, 6H). Chiral UPLC = 12.3 mins, 100% e.e. |
| 040 | 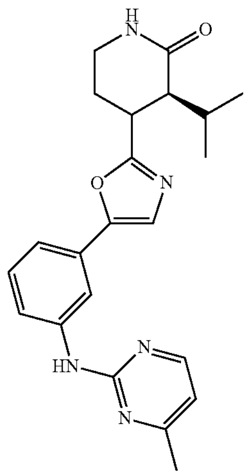 [SMILES: Cc1ccnc(Nc2cccc(-c3cnc(C4CCNC(=O)[C@H]4C(C)C)o3)c2)n1] | (R)-3-Isopropyl-4-{5-[3-(4-methyl-pyrimidin-2-ylamino)-phenyl]-oxazol-2-yl}-piperazin-2-one | ¹H NMR (400 MHz, DMSO) δ 9.58 (s, 1H), 8.33 (d, J = 5.0 Hz, 1H), 8.07 (s, 2H), 7.63 (d, J = 7.6 Hz, 1H), 7.27 (t, J = 8.4 Hz, 1H), 7.24 (s, 1H), 7.12 (d, J = 7.7 Hz, 1H), 6.75 (d, J = 5.0 Hz, 1H), 4.21 (d, J = 6.0 Hz, 1H), 3.98 (dt, J = 12.8, 4.2 Hz, 1H), 3.52 (ddd, J = 13.1, 8.9, 4.1 Hz, 1H), 3.43-3.35 (m, 1H), 3.30-3.14 (m, 1H), 2.41-2.33 (m, 4H), 1.06 (d, J = 6.8 Hz, 3H), 0.99 (d, J = 6.8 Hz, 3H). Chiral UPLC: r.t. = 10.1 mins, 99% e.e. |
| 041 | 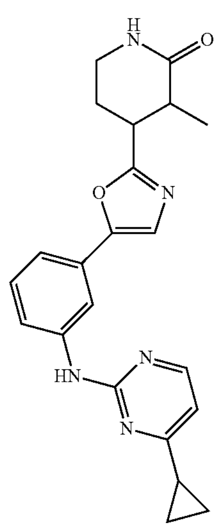 [SMILES: CC1C(=O)NCCC1c1ncc(-c2cccc(Nc3nccc(C4CC4)n3)c2)o1] | 4-{5-[3-(4-Cyclopropyl-pyrimidin-2-ylamino)-phenyl]-oxazol-2-yl}-3-methyl-piperazin-2-one | ¹H NMR (400 MHz, DMSO-$d_6$) δ 9.45 (s, 1H), 8.26 (d, J = 5.0 Hz, 1H), 8.12 (t, J = 1.8 Hz, 1H), 8.07 (d, J = 2.7 Hz, 1H), 7.46 (dd, J = 8.2, 1.2 Hz, 1H), 7.28-7.23 (m, 2H), 7.14-7.11 (m, 1H), 6.82 (d, J = 5.1 Hz, 1H), 4.44 (q, J = 6.9 Hz, 1H), 3.97 (dt, J = 13.5, 3.7 Hz, 1H), 3.56-3.48 (m, 1H), 3.44-3.36 (m, 1H), 3.28-3.24 (m, 1H), 2.04 (tt, J = 7.6, 4.9 Hz, 1H), 1.44 (d, J = 7.0 Hz, 3H), 1.17-0.99 (m, 4H). |

TABLE 1-continued

| Ex # | Chemical structure | Name | ¹H NMR/LCMS |
|---|---|---|---|
| 042 | 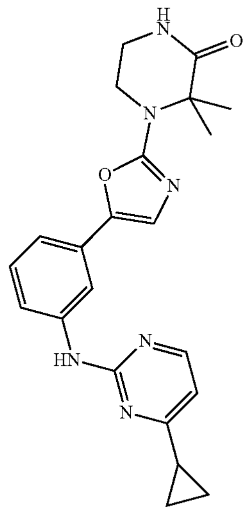 [SMILES: CC1(C)C(=O)NCCN1c1ncc(-c2cccc(Nc3nccc(C4CC4)n3)c2)o1] | 4-{5-[3-(4-Cyclopropyl-pyrimidin-2-ylamino)-phenyl]-oxazol-2-yl}-3,3-dimethyl-piperazin-2-one | ¹H NMR (400 MHz, DMSO-d₆) δ 9.50 (s, 1H), 8.26 (d, J = 5.1 Hz, 1H), 8.12 (t, J = 2.8 Hz, 1H), 8.08 (t, J= 1.8 Hz, 1H), 7.54 (dd, J = 8.1, 1.3 Hz, 1H), 7.31-7.22 (m, 2H), 7.17-7.06 (m, 1H), 6.81 (d, J = 5.1Hz, 1H), 3.74 (dd, J = 5.9, 4.3 Hz, 2H), 3.35-3.31 (m, 2H), 2.03 (tt, J = 7.9, 5.2 Hz, 1H), 1.67 (s, 6H), 1.10-1.02 (m, 4H). |
| 043 | 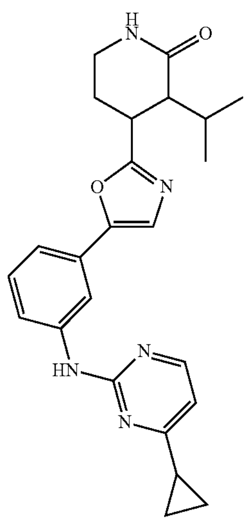 [SMILES: CC(C)C1C(=O)NCCC1c1ncc(-c2cccc(Nc3nccc(C4CC4)n3)c2)o1] | 4-{5-[3-(4-Cyclopropyl-pyrimidin-2-ylamino)-phenyl]-oxazol-2-yl}-3-isopropyl-piperazin-2-one | ¹H NMR (400 MHz, DMSO-d₆) δ 9.46 (s, 1H), 8.26 (d, J = 5.0 Hz, 1H), 8.07 (s, 2H), 7.50 (d, J = 8.0 Hz, 1H), 7.26 (t, J = 8.0 Hz, 1H), 7.23 (s, 1H), 7.11 (d, J = 7.7 Hz, 1H), 6.81 (d, J = 5.1 Hz, 1H), 4.23 (d, J = 6.0 Hz, 1H), 4.01 (dt, J = 8.7, 4.1 Hz, 1H), 3.53 (ddd, J = 13.0, 9.0, 4.2 Hz, 1H), 3.42-3.34 (m, 1H), 3.30-3.24 (m, 1H), 2.37 (td, J = 13.4, 6.5 Hz, 1H), 2.12-1.92 (m, 1H), 1.09-0.96 (m, 10H). |
| 044 | 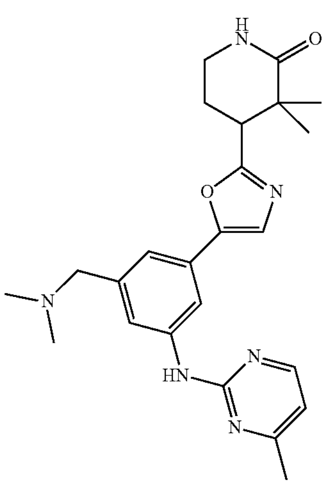 | 4-{5-[3-Dimethyl aminomethyl-5-(4-methyl-pyrimidin-2-ylamino)-phenyl]-oxazol-2-yl}-3,3-dimethyl-piperazin-2-one | ¹H NMR (400 MHz, DMSO-d₆) δ 9.59 (s, 1H), 8.33 (d, J = 5.0 Hz, 1H), 8.13 (s, 1H), 8.09 (t, J = 1.8 Hz, 1H), 7.51 (t, J = 1.8 Hz, 1H), 7.27 (s, 1H), 7.06 (d, J = 1.6 Hz, 1H), 6.75 (d, J = 5.0 Hz, 1H), 3.74-3.68 (m, 2H), 3.34-3.31 (m, 2H), 3.31 (s, 2H), 2.37 (s, 3H), 2.16 (s, 6H), 1.67 (s, 6H). |

TABLE 1-continued

| Ex # | Chemical structure | Name | ¹H NMR/LCMS |
|---|---|---|---|
| 045 | 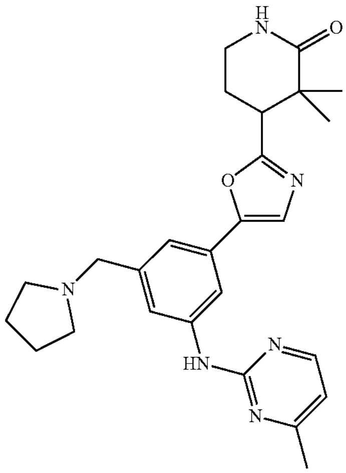 [SMILES: Cc1ccnc(Nc2cc(CN3CCCC3)cc(-c3cnc(C4CCNC(=O)C4(C)C)o3)c2)n1] | 3,3-Dimethyl-4-{5-[3-(4-methyl-pyrimidin-2-ylamino)-5-pyrrolidin-1-ylmethyl-phenyl]-oxazol-2-yl}-piperazin-2-one | 1H NMR (300 MHz, DMSO-$d_6$) δ 9.60 (s, 1H), 8.33 (d, J = 5.0 Hz, 1H), 8.16 (s, 1H), 8.07 (t, J = 1.8 Hz, 1H), 7.53 (t, J = 1.7 Hz, 1H), 7.28 (s, 1H), 7.07 (t, J = 1.5 Hz, 1H), 6.74 (d, J = 5.0 Hz, 1H), 3.72 (dd, J = 6.5, 3.7 Hz, 2H), 3.53 (s, 2H), 3.33-3.28 (m, 2H), 2.49-2.41 (m, 4H), 2.36 (s, 3H), 1.70 (t, J = 3.4 Hz, 4H), 1.67 (s, 6H). |

Biological Assays: In Vitro Syk Inhibition Assays

Protocol Inhibition Assays.

SYK kinase was purified as a full length protein in a baculovirus system near homogeneity. All kinase assays were performed with the Kinase TK (tyrosine kinase) HTRF (Homogeneous Time Resolved Fluorescence) assay developed by Cisbio international. These assays were carried out at room temperature in 96-wells half-area white plates in a final volume of 25 µl of kinase buffer (10 mM $MgCl_2$; 2 mM $MnCl_2$; 50 mM Sodium-HEPES pH 7.8; BRIJ-35 0.01%, 1 µM substrate) containing ATP at a concentration of at least twice the Km for each enzyme and an appropriate amount of recombinant enzyme to ensure a linear reaction rate. Reactions were initiated upon introduction of the enzyme and terminated with the addition of one reaction volume (25 µl) of HTRF detection buffer. Plates were incubated for one hour at room temperature and the time resolved Fluorescence resonance energy transfer signal was measured in a Pherastar FS microplate reader (BMG Labtech). All data are the average of triplicate results with a standard deviation <10%.

Experimental Results.

The experimental results for various compounds according to the invention using above-described protocols are set forth in table 2.

TABLE 2 in vitro inhibitions of various compounds against Syk

| $IC_{50}$ (microM) | Compounds |
|---|---|
| $IC_{50} \leq 0.1$ | 001, 002, 003, 004, 005, 007, 008, 009, 010, 011, 012, 013, 015, 017, 018, 019, 020, 021, 023, 025, 026, 036, 037, 038, 040, 041, 042, 043 |
| $0.1 < IC_{50} < 1$ | 014, 024, 027, 028, 030, 039, 044, 045 |
| $1 < IC_{50} < 10$ | 006, 016, 022, 029, 031, 032, 033, 034, 035 |

IC50: Concentration inhibiting 50% of protein kinase.

Comments on the Experiments and Results.

A very effective inhibition of Syk is observed by the class of compounds of formula (I) as herein disclosed. The listed compounds in table 1 are well representing the class of compounds of formula (I).

The invention claimed is:

1. A compound of formula (I):

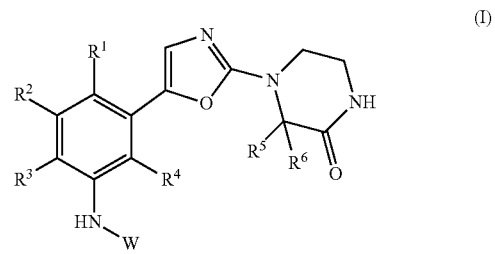

(I)

or a pharmaceutically acceptable salt thereof, wherein:
$R^1$, $R^2$, $R^3$, and $R^4$ are each independently selected from:
 hydrogen,
 cyano,
 haloalkyl,
 halogen,
 an alkyl group optionally substituted with a group selected from a heterocycle or —NRR',
 an alkoxy group optionally substituted with a group selected from a heterocycle or —NRR',
 a water-solubilising group,
 heterocycle,
 —CO—NRR',
 —$SO_2$—NRR',
 —NRR',
 —NR—CO—R', or
 a —NR—$SO_2$R' group;
 wherein R and R' are each independently selected from hydrogen or an alkyl group;
$R^5$ is an alkyl group optionally substituted with a group selected from heterocycle, hydroxyl, cyano, amino, or alkoxy;
$R^6$ is selected from hydrogen, an alkyl group, or a cycloalkyl group;
W is selected from aryl or heteroaryl groups, the aryl or heteroaryl groups being optionally substituted by one or more substituents selected from:
 cyano, haloalkyl,
halogen,
an alkyl group optionally substituted with a heterocycle,
a cycloalkyl group,
an alkoxy group optionally substituted with a heterocycle,
an aryl group,
a heteroaryl group,
a heterocycloalkyl group optionally substituted with an alkyl group,
a water-solubilising group,
—CO—NRR',
—SO$_2$—NRR',
—NRR',
—NR—CO—R', or
a —NR—SO$_2$R' group;
wherein R and R' are each independently selected from hydrogen or alkyl group,
wherein the water-solubilising group is selected from:
N—(CH$_2$)$_z$R''',
N—(CH$_2$)$_z$—C(O)R''',
N—(CH$_2$)$_z$—C(O)OR''',
N—(CH$_2$)$_z$—S(O)$_2$R''',
N—(CH$_2$)$_z$—S(O)$_2$OR''',
N—(CH$_2$)$_z$—C(O)NR''R''',
or one of the following structures (a)-(k):

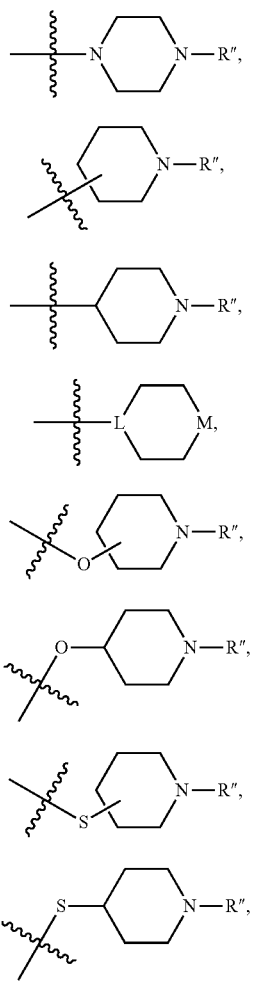

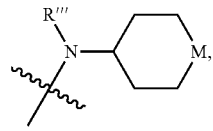

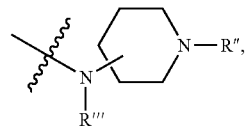

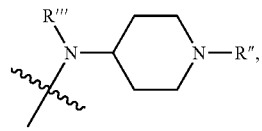

wherein:
L is selected from CH or N;
M is selected from —CH(R'')—, —CH$_2$—, —O—, —S—, —NH—, —N(—(CH$_2$)$_z$—R'')—, —N(—(CH$_2$)$_z$—C(O)R'')—, —N(—(CH$_2$)$_z$—C(O)OR'')—, —N(—(CH$_2$)$_z$—S(O)$_2$R'')—, —N(—(CH$_2$)$_z$—S(O)$_2$OR'')— or —N(—(CH$_2$)$_z$—C(O)NR''R''')—,
with the proviso that L and M are not both simultaneously CH and CH$_2$, respectively;
z is an integer ranging from 0 to 6;
R'' and R''' are each independently selected from: hydrogen; a C$_1$-C$_{10}$ alkyl group which is optionally substituted with one or more heteroatoms selected from F, Cl, Br, I, O, and N; a C$_1$-C$_{10}$ alkoxy group; an unsubstituted aryl; or an unsubstituted heteroaryl.

2. The compound according to claim 1, or a pharmaceutically acceptable salt thereof, wherein W is a substituted heteroaryl.

3. The compound according to claim 1, or a pharmaceutically acceptable salt thereof, wherein W is a 5-8 membered, monosubstituted or disubstituted, monocyclic ring containing at least one nitrogen atom.

4. The compound according to claim 1, or a pharmaceutically acceptable salt thereof, wherein at least three of R$^1$, R$^2$, R$^3$ and R$^4$ are hydrogen.

5. The compound according to claim 1, of formula (II),

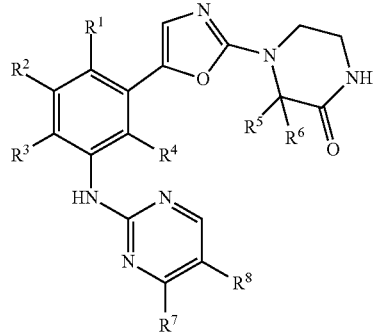

or a pharmaceutically acceptable salt thereof,
wherein R$^7$ and R$^8$ are each independently selected from:
hydrogen, cyano,
CF₃,
halogen,
an alkyl group optionally substituted with a heterocycle,
a cycloalkyl group,
an alkoxy group optionally substituted with a heterocycle,
an aryl group,
a heteroaryl group,
a heterocycloalkyl group optionally substituted with an alkyl group,
a water-solubilising group, or
—NRR', wherein R and R' are each independently selected from hydrogen or an alkyl group; and
the water-solubilising group is selected from:
N—(CH₂)$_z$R",
N—(CH₂)$_z$—C(O)R",
N—(CH₂)$_z$—C(O)OR",
N—(CH₂)$_z$—S(O)₂R",
N—(CH₂)$_z$—S(O)₂OR",
N—(CH₂)$_z$—C(O)NR"R''',
or one of the following structures (a)-(k):

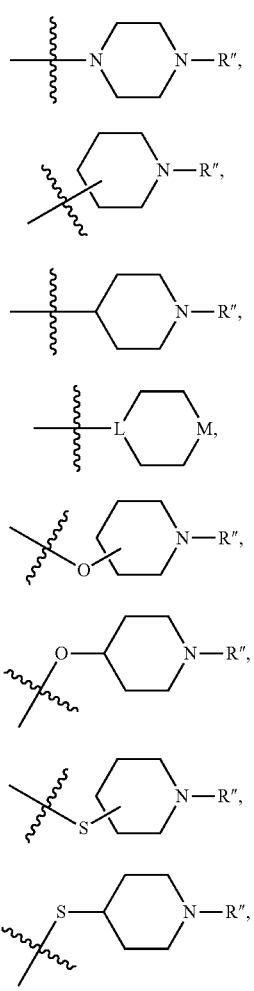

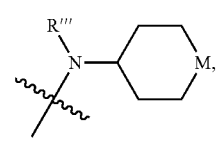

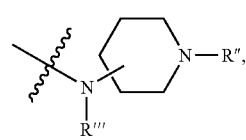

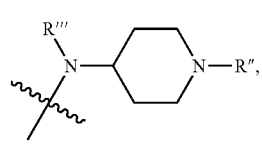

wherein:
L is selected from CH or N;
M is selected from —CH(R")—, —CH₂—, —O—, —S—, —NH—, —N(—(CH₂)$_z$—R")—, —N(—(CH₂)$_z$—C(O)R")—, —N(—(CH₂)$_z$—C(O)OR")—, —N(—(CH₂)$_z$—S(O)₂R")—, —N(—(CH₂)$_z$—S(O)₂OR")— or —N(—(CH₂)$_z$—C(O)NR"R''')—, with the proviso that L and M are not both simultaneously CH and CH₂, respectively;
z is an integer ranging from 0 to 6;
R" and R''' are each independently selected from: hydrogen; a C₁-C₁₀ alkyl group which is optionally substituted with one or more heteroatoms selected from F, Cl, Br, I, O, and N; a C₁-C₁₀ alkoxy group; an unsubstituted aryl; or an unsubstituted heteroaryl.

6. The compound according to claim 5, of formula (III),

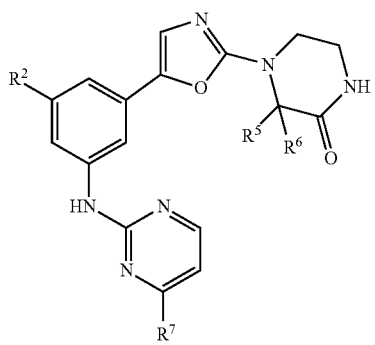

or a pharmaceutically acceptable salt thereof.

7. The compound according to claim 1, selected from:
3-Methyl-4-{5-[3-(4-methyl-pyrimidin-2-ylamino)-phenyl]-oxazol-2-yl}-piperazin-2-one;
3,3-Dimethyl-4-{5-[3-(4-methyl-pyrimidin-2-ylamino)-phenyl]-oxazol-2-yl}-piperazin-2-one;
3-Isopropyl-4-{5-[3-(4-methyl-pyrimidin-2-ylamino)-phenyl]-oxazol-2-yl}-piperazin-2-one;
4-{5-[3-(4-Ethyl-pyrimidin-2-ylamino)-phenyl]-oxazol-2-yl}-3-methyl-piperazin-2-one;
3,3-Dimethyl-4-{5-[3-(4-methyl-pyrimidin-2-ylamino)-5-morpholin-4-ylmethyl-phenyl]-oxazol-2-yl}-piperazin-2-one;

3-Methyl-4-{5-[3-(5-propyl-pyrimidin-2-ylamino)-phenyl]-oxazol-2-yl}-piperazin-2-one;
(R)-3-Methyl-4-{5-[3-(4-methyl-pyrimidin-2-ylamino)-phenyl]-oxazol-2-yl}-piperazin-2-one;
2-{3-[2-(2-Methyl-3-oxo-piperazin-1-yl)-oxazol-5-yl]-5-(morpholin-4-ylmethyl)-phenylamino}-pyrimidine-4-carbonitrile;
3-Methyl-4-{5-[3-((4-trifluoromethyl)-pyrimidin-2-ylamino)-phenyl]-oxazol-2-yl}-piperazin-2-one;
3-Methyl-4-{5-[3-(4-thiophen-2-yl-pyrimidin-2-ylamino)-phenyl]-oxazol-2-yl}-piperazin-2-one;
3-Ethyl-4-{5-[3-((4-trifluoromethyl)-pyrimidin-2-ylamino)-phenyl]-oxazol-2-yl}-piperazin-2-one;
3-Isopropyl-4-{5-[3-((4-trifluoromethyl)-pyrimidin-2-ylamino)-phenyl]-oxazol-2-yl}-piperazin-2-one;
4-{5-[3-(4-Methoxy-pyrimidin-2-ylamino)-phenyl]-oxazol-2-yl}-3-methyl-piperazin-2-one;
3-Methyl-4-{5-[3-(4-methyl-pyrimidin-2-ylamino)-5-morpholin-4-ylmethyl-phenyl]-oxazol-2-yl}-piperazin-2-one;
3-Methyl-4-{5-[3-morpholin-4-ylmethyl-5-((4-trifluoromethyl)-pyrimidin-2-ylamino)-phenyl]-oxazol-2-yl}-piperazin-2-one;
4-{5-[3-(5-Ethyl-pyrimidin-2-ylamino)-phenyl]-oxazol-2-yl}-3-methyl-piperazin-2-one;
2-{3-[2-(2-Methyl-3-oxo-piperazin-1-yl)-oxazol-5-yl]-phenylamino}-pyrimidine-4-carbonitrile;
3,3-Dimethyl-4-{5-[3-((4-trifluoromethyl)-pyrimidin-2-ylamino)-phenyl]-oxazol-2-yl}-piperazin-2-one;
(S)-3-Methyl-4-{5-[3-(4-methyl-pyrimidin-2-ylamino)-phenyl]-oxazol-2-yl}-piperazin-2-one;
3-Ethyl-4-{5-[3-(4-methyl-pyrimidin-2-ylamino)-phenyl]-oxazol-2-yl}-piperazin-2-one;
4-{5-[3-(4-Isopropyl-pyrimidin-2-ylamino)-phenyl]-oxazol-2-yl}-3-methyl-piperazin-2-one;
4-{5-[3-(4,5-Dimethyl-pyrimidin-2-ylamino)-phenyl]-oxazol-2-yl}-3,3-dimethyl-piperazin-2-one;
4-{5-[3-(4-Isopropyl-pyrimidin-2-ylamino)-phenyl]-oxazol-2-yl}-3,3-dimethyl-piperazin-2-one;
3-(2-Hydroxy-ethyl)-4-{5-[3-(4-methyl-pyrimidin-2-ylamino)-phenyl]-oxazol-2-yl}-piperazin-2-one;
3-Ethyl-4-{5-[3-(4-isopropyl-pyrimidin-2-ylamino)-phenyl]-oxazol-2-yl}-piperazin-2-one;
4-{5-[3-(4-Methoxy-pyrimidin-2-ylamino)-phenyl]-oxazol-2-yl}-3,3-dimethyl-piperazin-2-one;
3-Methyl-4-{5-[3-(4-morpholin-4-yl-pyrimidin-2-ylamino)-phenyl]-oxazol-2-yl}-piperazin-2-one;
3-Methyl-4-{5-[3-(4-pyrrolidin-1-yl-pyrimidin-2-ylamino)-phenyl]-oxazol-2-yl}-piperazin-2-one;
3-Methyl-4-(5-{3-[4-(4-methyl-piperazin-1-yl)-pyrimidin-2-ylamino]-phenyl}-oxazol-2-yl)-piperazin-2-one;
3,3-Dimethyl-4-{5-[3-(4-morpholin-4-yl-pyrimidin-2-ylamino)-phenyl]-oxazol-2-yl}-piperazin-2-one;
3,3-Dimethyl-4-(5-{3-[4-(4-methyl-piperazin-1-yl)-pyrimidin-2-ylamino]-phenyl}-oxazol-2-yl)-piperazin-2-one;
3,3-Dimethyl-4-{5-[3-(4-pyrrolidin-1-yl-pyrimidin-2-ylamino)-phenyl]-oxazol-2-yl}-piperazin-2-one;
3-Isopropyl-4-{5-[3-(4-morpholin-4-yl-pyrimidin-2-ylamino)-phenyl]-oxazol-2-yl}-piperazin-2-one;
3-Isopropyl-4-{5-[3-(4-pyrrolidin-1-yl-pyrimidin-2-ylamino)-phenyl]-oxazol-2-yl}-piperazin-2-one;
3-Isopropyl-4-(5-{3-[4-(4-methyl-piperazin-1-yl)-pyrimidin-2-ylamino]-phenyl}-oxazol-2-yl)-piperazin-2-one;
3-Isopropyl-4-{5-[3-(4-isopropyl-pyrimidin-2-ylamino)-phenyl]-oxazol-2-yl}-piperazin-2-one;
4-{5-[3-(4-Ethyl-pyrimidin-2-ylamino)-phenyl]-oxazol-2-yl}-3,3-dimethyl-piperazin-2-one;
4-{5-[3-(4-Ethyl-pyrimidin-2-ylamino)-phenyl]-oxazol-2-yl}-3-isopropyl-piperazin-2-one;
(S)-3-Isopropyl-4-{5-[3-(4-methyl-pyrimidin-2-ylamino)-phenyl]-oxazol-2-yl}-piperazin-2-one;
(R)-3-Isopropyl-4-{5-[3-(4-methyl-pyrimidin-2-ylamino)-phenyl]-oxazol-2-yl}-piperazin-2-one;
4-{5-[3-(4-Cyclopropyl-pyrimidin-2-ylamino)-phenyl]-oxazol-2-yl}-3-methyl-piperazin-2-one;
4-{5-[3-(4-Cyclopropyl-pyrimidin-2-ylamino)-phenyl]-oxazol-2-yl}-3,3-dimethyl-piperazin-2-one;
4-{5-[3-(4-Cyclopropyl-pyrimidin-2-ylamino)-phenyl]-oxazol-2-yl}-3-isopropyl-piperazin-2-one;
4-{5-[3-Dimethyl aminomethyl-5-(4-methyl-pyrimidin-2-ylamino)-phenyl]-oxazol-2-yl}-3,3-dimethyl-piperazin-2-one; or
3,3-Dimethyl-4-{5-[3-(4-methyl-pyrimidin-2-ylamino)-5-pyrrolidin-1-ylmethyl-phenyl]-oxazol-2-yl}-piperazin-2-one;
and/or a pharmaceutically acceptable salt thereof.

8. A pharmaceutical composition comprising a compound according to claim 1 and at least one pharmaceutically acceptable excipient and/or carrier.

9. The pharmaceutical composition according to claim 8, wherein the compound is the sole active pharmaceutical ingredient.

10. The pharmaceutical composition according to claim 8, comprising the compound in combination with another active pharmaceutical ingredient.

11. A method for treating a disease or disorder associated with unregulated tyrosine kinase activity comprising a step of administration to a subject in need thereof of a compound according to claim 1.

12. The method according to claim 11, wherein the disease or disorder associated with unregulated tyrosine kinase activity is selected from hematological disorders, proliferative disorders, autoimmune disorders, metabolic disorders, inflammatory diseases, allergic diseases, or neurological diseases.

13. The method according to claim 11, further comprising a step of administration of another active pharmaceutical ingredient to the subject in need thereof, the other active pharmaceutical ingredient being administered by sequential administration with the compound.

14. The method according to claim 11, further comprising a step of administration of another active pharmaceutical ingredient to the subject in need thereof, the other active pharmaceutical ingredient being administered by simultaneous administration with the compound.

15. The method according to claim 11, further comprising a step of administration of another active pharmaceutical ingredient to the subject in need thereof, the other active pharmaceutical ingredient being administered by separate administration with the compound.

* * * * *